United States Patent
Faler et al.

(10) Patent No.: US 10,252,967 B2
(45) Date of Patent: Apr. 9, 2019

(54) BRIDGED BI-AROMATIC LIGANDS AND TRANSITION METAL COMPOUNDS PREPARED THEREFROM

(71) Applicant: Univation Technologies, LLC, Houston, TX (US)

(72) Inventors: Catherine Anne Faler, Houston, TX (US); Kevin P. Ramirez, Houston, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 15/567,666

(22) PCT Filed: Apr. 19, 2016

(86) PCT No.: PCT/US2016/028293
§ 371 (c)(1),
(2) Date: Oct. 19, 2017

(87) PCT Pub. No.: WO2016/172110
PCT Pub. Date: Oct. 27, 2016

(65) Prior Publication Data
US 2018/0086685 A1   Mar. 29, 2018

Related U.S. Application Data

(60) Provisional application No. 62/150,131, filed on Apr. 20, 2015.

(51) Int. Cl.
| | | |
|---|---|---|
| *C07C 43/13* | (2006.01) | |
| *C07C 41/01* | (2006.01) | |
| *C07C 41/30* | (2006.01) | |
| *C07C 41/26* | (2006.01) | |
| *C08F 10/02* | (2006.01) | |
| *B01J 31/38* | (2006.01) | |
| *C08F 10/00* | (2006.01) | |
| *C07C 43/178* | (2006.01) | |
| *C07C 43/23* | (2006.01) | |
| *C07F 7/00* | (2006.01) | |
| *C08F 110/06* | (2006.01) | |

(52) U.S. Cl.
CPC ............ *C07C 43/135* (2013.01); *B01J 31/38* (2013.01); *C07C 41/01* (2013.01); *C07C 41/26* (2013.01); *C07C 41/30* (2013.01); *C07C 43/1783* (2013.01); *C07C 43/1785* (2013.01); *C07C 43/23* (2013.01); *C07F 7/003* (2013.01); *C08F 10/00* (2013.01); *C08F 10/02* (2013.01); *C08F 110/06* (2013.01)

(58) Field of Classification Search
CPC ....... C07C 41/26; C07C 43/135; C07C 41/01; C07C 41/30; C08F 10/02
See application file for complete search history.

(56) References Cited

U.S. PATENT DOCUMENTS 8,722,819 B2 * 5/2014 Robert .................... C08F 10/00
526/129
2013/0090438 A1   4/2013 Dominique et al.

OTHER PUBLICATIONS

International Preliminary Report on Patentability for related PCT Application PCT/US2016/028293, dated Nov. 2, 2017 (8 pgs).
Uraguchi, et al., Chiral Ammonium Betaines: A Bifunctional Organic Base Catalyst for Asymmetric Mannich-Type Reaction of .alpha.-Nitrocaboxylates; Journal of the American Chemical Society, vol. 130 (Jan. 1, 2008) (2 pgs).
International Search Report & Written Opinion for related PCT Application PCT/US2016/028293, dated Jun. 24, 2016 (12 pgs).

* cited by examiner

*Primary Examiner* — Rosalynd A Keys
(74) *Attorney, Agent, or Firm* — Brooks, Cameron & Huebsch, PLLC

(57) ABSTRACT

Disclosed are novel bridged bi-aromatic phenol ligands and transition metal compounds derived therefrom. Also disclosed are methods of making the ligands and transition metal compounds.

20 Claims, 10 Drawing Sheets

(1)

(2)

(3)

(4)

(5)

(6)

(7)

(8)

(9)

(10)

(12)

(13)

(14)

(15)

(16)

(17)

(18)

(19)

(20)

(21)

(22)

(23)

BRIDGED BI-AROMATIC LIGANDS AND TRANSITION METAL COMPOUNDS PREPARED THEREFROM

This application is a National Stage Application under 35 U.S.C. § 371 of International Application Number PCT/US2016/028293, filed Apr. 19, 2016 and published as WO 2016/172110 on Oct. 27, 2016, which claims the benefit to U.S. Provisional Application 62/150,131, filed Apr. 20, 2015, the entire contents of which are incorporated herein by reference in its entirety.

FIELD

The present disclosure is directed to bridged bi-aromatic ligands and transition metal compounds prepared therefrom. The disclosure is also directed to methods of preparing the ligands and transition metal compounds.

BACKGROUND

A major focus of the polyolefin industry in recent years has been on the development of new catalysts that deliver new and improved products. Bulky ligand transition metal compounds, for example, are now widely utilized in catalyst compositions to produce polyolefin polymers, such as polyethylene polymers.

It is recognized in the art that small differences in the molecular structure of a catalyst compound can greatly impact catalyst performance and that this is often governed by ligand structure. Therefore considerable effort has been expended in designing new ligand structures that may lead to catalysts of enhanced performance. WO 03/09162 discloses bridged bi-aromatic ligands, methods for their preparation and transition metal compounds derived therefrom.

It would be desirable to provide new bridged bi-aromatic ligands and methods for their synthesis. It would also be desirable to provide new transition metal compounds based on the new ligand structures.

SUMMARY

In one aspect there is provided a bridged bi-aromatic phenol ligand of formula (I):

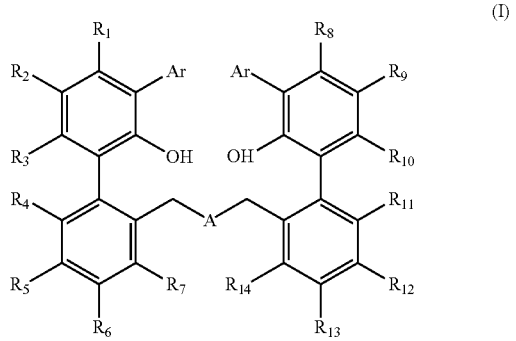

(I)

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is O, S, $NR^a$ and $PR^a$ wherein $R^a$ is optionally substituted hydrocarbyl, or A is —Y-E-Y'— wherein E is a bridging group having from one to 50 non-hydrogen atoms and Y and Y' are independently selected from O, S, $NR^a$ and $PR^a$ wherein $R^a$ is optionally substituted hydrocarbyl; Ar is, independently, optionally substituted aryl or optionally substituted heteroaryl.

Each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be independently selected from the group consisting of hydride, halide, and optionally substituted alkyl, heteroalkyl, aryl, heteroaryl, alkoxyl, aryloxyl, silyl, dialkylamino, alkylthio, and arylthio.

Each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be independently selected from the group consisting of hydride, halide, and optionally substituted alkyl, heteroalkyl, aryl, heteroaryl, alkoxyl, and aryloxyl.

The bridging group E may be selected from the group consisting of optionally substituted divalent hydrocarbyl and divalent heteroatom containing hydrocarbyl.

The bridging group E may be selected from the group consisting of optionally substituted divalent alkyl, alkenyl, alkynyl, heteroalkyl, heteroalkenyl, heteroalkynyl, carbocycle, heterocarbocycle, aryl, heteroaryl and silyl.

The bridging group E may be represented by the general formula $-(QR^{15}_{2-z''})_{z'}-$ wherein each Q is either carbon or silicon and each $R^{15}$ may be the same or different from the others such that each $R^{15}$ is selected from the group consisting of hydride and optionally substituted hydrocarbyl and heteroatom containing hydrocarbyl, and optionally two or more $R^{15}$ groups may be joined into a ring structure having from 3 to 50 atoms in the ring structure not counting hydrogen atoms; z' is an integer from 1 to 10; and z" is 0, 1 or 2.

In any one of the hereinbefore disclosed embodiments Ar may be, independently, an optionally substituted phenyl, naphthyl, biphenyl, anthracenyl or phenanthrenyl.

In any one of the hereinbefore disclosed embodiments Ar may be, independently, an optionally substituted thiophene, pyridine, isoxazole, pyrazole, pyrrole, furan, or benzo-fused analogues of these rings.

In any one of the hereinbefore disclosed embodiments each occurrence of Ar may be the same.

The bridged bi-aromatic phenol ligand of formula (I) may be of formula (II):

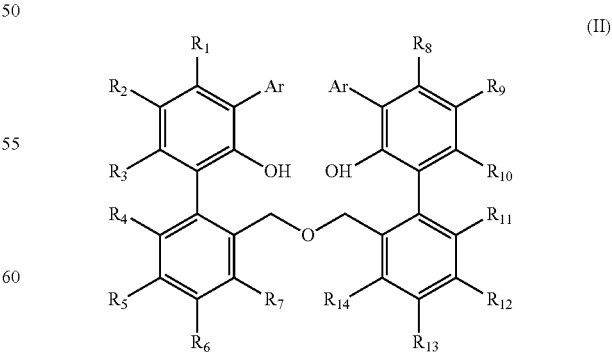

(II)

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and Ar is as defined in any one of the hereinbefore disclosed embodiments.

The bridged bi-aromatic phenol ligand of formula (I) may be of formula (III):

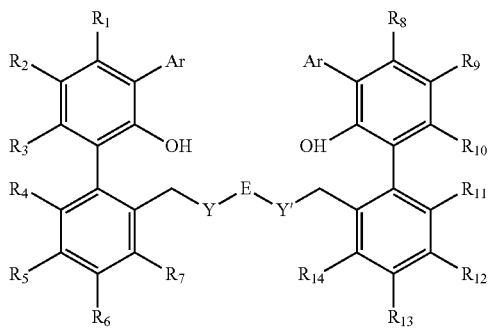

(III)

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, Ar, Y, Y' and E is as defined in any one of the hereinbefore disclosed embodiments.

The bridged bi-aromatic phenol ligand of formula (I) may be of formula (IV):

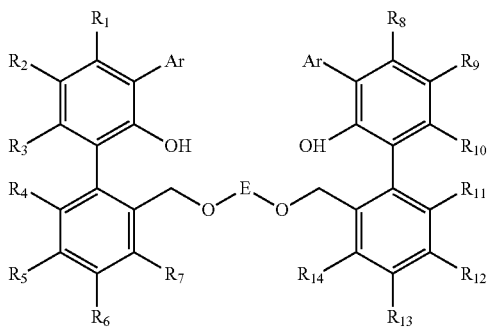

(IV)

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, Ar, and E is as defined in any one of the hereinbefore disclosed embodiments.

In another aspect there is provided a method of preparing a bridged bi-aromatic phenol ligand of formula (I), (II), (III) or (IV) comprising at least one step of directly ortho lithiating the aromatic ring of a protected phenol; wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is O, S, $NR^a$ or $PR^a$ wherein $R^a$ is optionally substituted hydrocarbyl, or A is —Y-E-Y'— wherein E is a bridging group having from one to 50 non-hydrogen atoms; Y and Y' are independently selected from O, S, $NR^a$ and $PR^a$ wherein $R^a$ is optionally substituted hydrocarbyl; Ar is optionally substituted aryl or heteroaryl.

By 'directly ortho lithiating the aromatic ring of a protected phenol' it is meant that the position in an aromatic ring ortho to a protected phenol may be lithiated in a single step and without the need for an intermediate, such as a halogenated intermediate.

The method may comprise at least two steps of directly ortho-lithiating the aromatic ring of a protected phenol.

The method may also comprise at least one step of aryl coupling. The method may comprise at least one step of Negishi coupling. The method may comprise at least one step of Suzuki coupling. The method may comprise both at least one step of Negishi coupling and at least one step of Suzuki coupling.

The method may comprise the steps of:
a) treating a protected bi-aromatic phenol of formula (V) with a lithiating agent to yield a dilithio protected bi-aromatic phenol of formula (VI);

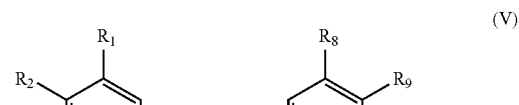

(V)

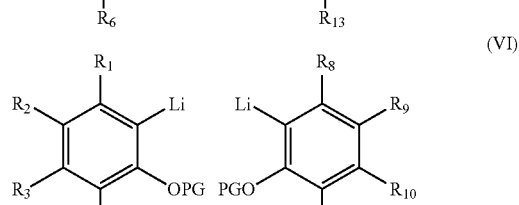

(VI)

b) treating the dilithio protected bi-aromatic phenol of formula (VI) with a zinc compound and a compound of formula ArX in the presence of a catalyst, to yield a protected bi-aromatic phenol of formula (VIII); and

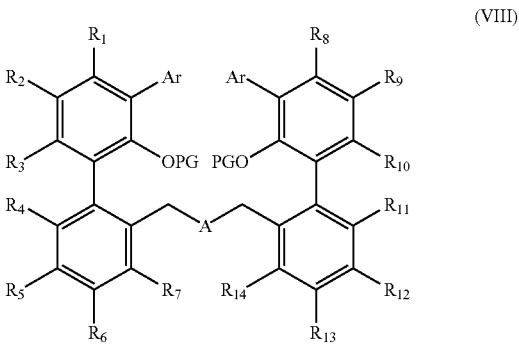

(VIII)

c) deprotecting the compound of formula (VIII) to yield the bi-aromatic phenol ligand of formula (I);
wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more $R^1$ to $R^{14}$ groups can combine together into ring structures with such ring structures having from 3 to 100 non-hydrogen atoms in the ring; A is O, S, $NR^a$ and $PR^a$ wherein $R^a$ is optionally substituted hydrocarbyl, or A is —Y-E-Y'— wherein E is a bridging group having from one to 50 non-hydrogen atoms; Y and Y' are independently selected from O, S, $NR^a$ and $PR^a$ wherein $R^a$ is optionally substituted hydrocarbyl; Ar is optionally substituted aryl or heteroaryl; X is halide; PG is a protecting group.

The method may comprise the steps of:
a) treating the dilithio protected bi-aromatic phenol of formula (VI) with a zinc halide to yield a zinc halide salt of the protected bi-aromatic phenol of formula (IX); and

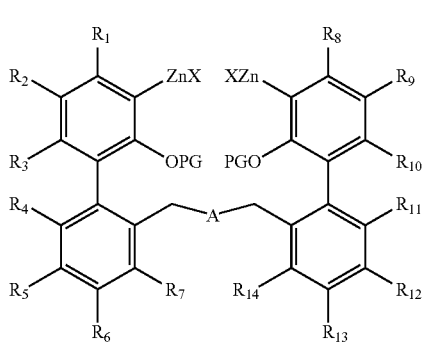
(IX)

b) treating the zinc halide salt of the protected bi-aromatic phenol of formula (IX) with a compound of formula ArX in the presence of a catalyst to yield a compound of formula (VIII).

The method may comprise the steps of:
a) treating a compound of formula (X) with a zinc halide and a compound of formula ArX in the presence of a catalyst to yield a compound of formula (XI);

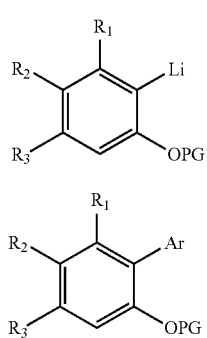
(X)

(XI)

b) treating the compound of formula (XI) with a lithiating agent to yield a compound of formula (XII);

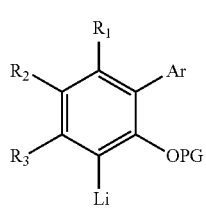
(XII)

c) treating the compound of formula (XII) with zinc halide and a compound of formula (XIII) in the presence of a catalyst to yield the compound of formula (VIII); and

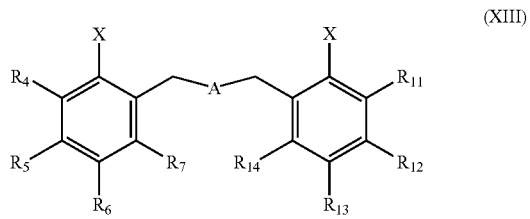
(XIII)

d) deprotecting the compound of formula (VIII) to yield the bi-aromatic phenol ligand of formula (I) wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ and independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is O, S, $NR^a$ and $PR^a$ wherein $R^a$ is optionally substituted hydrocarbyl, or A is —Y-E-Y'— wherein E is a bridging group having from one to 50 non-hydrogen atoms; Y and Y' are independently selected from O, S, $NR^a$ and $PR^a$ wherein $R^a$ is optionally substituted hydrocarbyl; Ar is optionally substituted aryl or heteroaryl; X is halide; PG is a protecting group.

The method may comprise the steps of:
a) treating the compound of formula (X) with zinc halide to yield a compound of formula (XIV); and

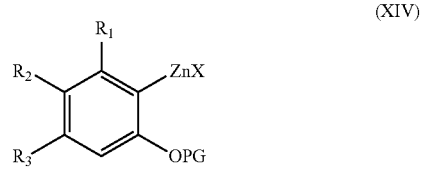
(XIV)

b) treating the zinc halide salt of formula (XIV) with a compound of formula ArX in the presence of a catalyst to yield the compound of formula (XI).

The method comprise the steps of:
a) treating the compound of formula (XII) with zinc halide to yield a compound of formula (XV); and

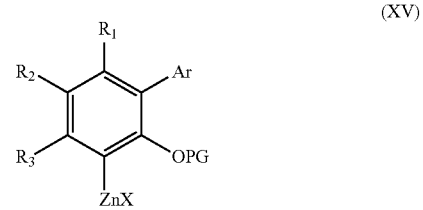
(XV)

b) treating the zinc halide salt of formula (XI) with a compound of formula (XIII) in the presence of a catalyst to yield a compound of formula (VIII).

In any one of the aforementioned embodiments the compound of formula (X) may be prepared by treating a compound of formula (XVI) with a lithiating agent;

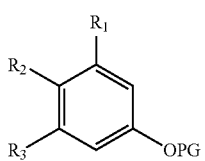

(XVI)

wherein PG is as hereinbefore defined.

In any one of the hereinbefore disclosed embodiments each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be independently selected from the group consisting of hydride, halide, and optionally substituted alkyl, heteroalkyl, aryl, heteroaryl, alkoxyl, aryloxyl, silyl, dialkylamino, alkylthio, and arylthio.

In any one of the hereinbefore disclosed embodiments each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be independently selected from the group consisting of hydride, halide, and optionally substituted alkyl, heteroalkyl, aryl, heteroaryl, alkoxyl, and aryloxyl.

In any one of the hereinbefore disclosed embodiments the bridging group E may be selected from the group consisting of optionally substituted divalent hydrocarbyl and divalent heteroatom containing hydrocarbyl.

In any one of the hereinbefore disclosed embodiments the bridging group E may be selected from the group consisting of optionally substituted divalent alkyl, alkenyl, alkynyl, heteroalkyl, heteroalkenyl, heteroalkynyl, carbocycle, heterocarbocycle, aryl, heteroaryl and silyl.

In any one of the hereinbefore disclosed embodiments the bridging group E may be represented by the general formula -(QR$^{15}_{2-z''}$)$_{z'}$— wherein each Q is either carbon or silicon and each $R^{15}$ may be the same or different from the others such that each $R^{15}$ is selected from the group consisting of hydride and optionally substituted hydrocarbyl and heteroatom containing hydrocarbyl, and optionally two or more $R^{15}$ groups may be joined into a ring structure having from 3 to 50 atoms in the ring structure not counting hydrogen atoms; z' is an integer from 1 to 10; and z" is 0, 1 or 2.

In any one of the hereinbefore disclosed embodiments Ar may be optionally substituted phenyl, naphthyl, biphenyl, anthracenyl, and phenanthrenyl.

In any one of the hereinbefore disclosed embodiments Ar may be thiophene, pyridine, isoxazole, pyrazole, pyrrole, furan or benzo-fused analogues of these rings.

In any one of the hereinbefore disclosed embodiments the protecting group PG may be a protecting group including, but not limited to: methyl (Me), benzyl (Bn), substituted benzyl, for example, 2-methoxyphenylmethyl (MPM), alkoxymethyl, for example, methoxymethyl (MOM), tetrahydropyranyl (THP), silyl, for example, trimethylsilyl (TMS) or tert-butyldimethylsilyl (TBS) and allyl. PG may be tetrahydropyranyl (THP) or methoxymethyl.

In any one of the hereinbefore disclosed embodiments lithiation may be performed with an alkyl or aryl lithium compound.

In any one of the hereinbefore disclosed embodiments any one of the disclosed lithium containing compounds may have one or more of its lithium atoms coordinated with one or more Lewis bases. The Lewis bases may be an ether or a cyclic ether.

In any one of the hereinbefore disclosed embodiments the zinc compound may comprise a zinc halide or zinc alkyl In any one of the hereinbefore disclosed embodiments the zinc halide may comprise zinc (II) chloride.

In any one of the hereinbefore disclosed embodiments the catalyst may comprise a nickel or palladium catalyst.

In any one of the hereinbefore disclosed embodiments the palladium catalyst may comprise a palladium phosphine catalyst. The palladium catalyst may comprise, for example, bis(tri-tert-butylphosphine)palladium, tetrakis(triphenylphosphine)palladium(0) (Pd(PPh$_3$)$_4$), bis[1,2-bis(diphenylphosphino)ethane]palladium(0) (Pd(dppe)$_2$), 1,1'-bis(diphenylphosphino)ferrocene palladium (Pd(dppf)), (2,2'-bis(diphenylphosphino)-1,1'-binaphthyl palladium (Pd (BINAP).

In any one of the hereinbefore disclosed embodiments the palladium phosphine catalyst may comprise bis(tri-tert-butylphosphine)palladium.

In any one of the hereinbefore disclosed embodiments deprotection may comprise treatment with acid. The acid may be any protic acid. Exemplary acids include hydrochloric acid or p-toluene sulfonic acid.

The herein disclosed methods may comprise any combination of the hereinbefore disclosed embodiments.

In another aspect there is provided a ligand of formula (I), (II), (III) and (IV) prepared by any one of the hereinbefore disclosed methods.

In another aspect there is provided a transition metal compound formed from any one of the ligands of formula (I), (II), (III) and (IV). The transition metal compounds may comprise a titanium, a zirconium or a hafnium atom.

In another aspect there is provided a catalyst composition comprising one or more transition metal compounds as hereinbefore disclosed, and one or more activators. The activator may comprise one or more alumoxanes. The activator may comprise methylalumoxane.

In another aspect there is provided a supported catalyst composition comprising one or more transition metal compounds as hereinbefore disclosed, one or more activators and one or more support materials. The activator may comprise one or more alumoxanes. The activator may comprise methylalumoxane. The support may be silica.

The catalyst composition or supported catalyst composition may comprise two or more transition metal compounds. The transition metal compounds may be selected from any one of those hereinbefore described or at least one of the transition metal compounds may be different from those hereinbefore described. For example, at least one of the transition metal compounds may be a metallocene.

In another aspect there is provided a process for polymerizing olefins, the process comprising: contacting olefins with one or more catalyst compositions or supported catalyst compositions comprising at least one transition metal compound as hereinbefore disclosed in a reactor under polymerization conditions to produce an olefin polymer or copolymer

DETAILED DESCRIPTION

Figure 1:
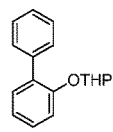
FIGS. 1 and 2 depict the chemical structures of exemplary compounds in accordance with the present disclosure.
Figure 1:
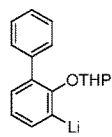
Figure 1:
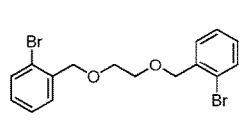
Figure 1:
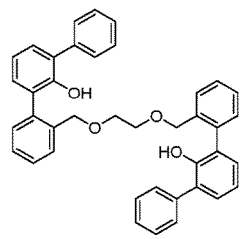
Figure 1:
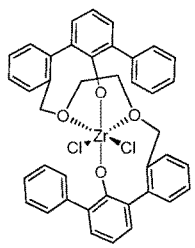
Figure 1:
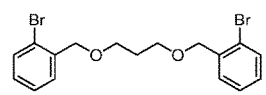
Figure 1:
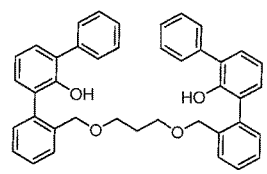
Figure 1:
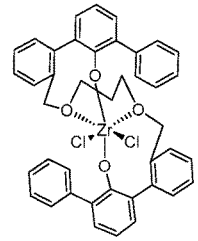
Figure 1:
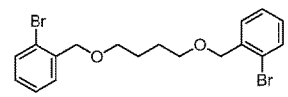
Figure 1:
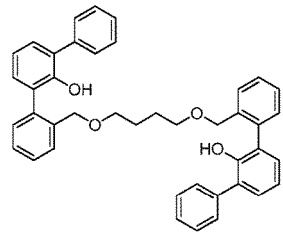
Figure 1:
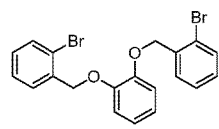
Figure 1:
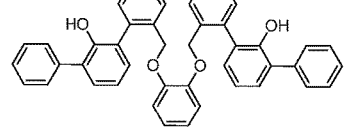
Figure 2:
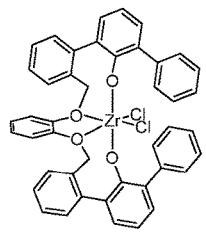
Figure 2:
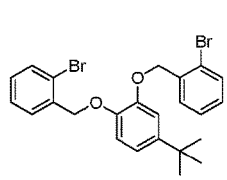
Figure 2:
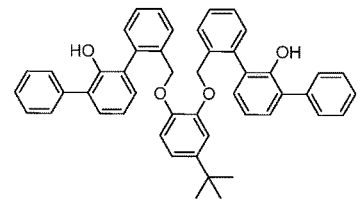
Figure 2:
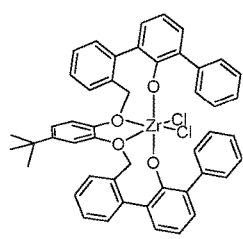
Figure 2:
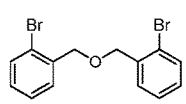
Figure 2:
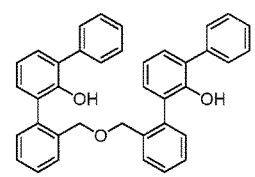
Figure 2:
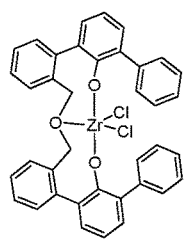
Figure 2:
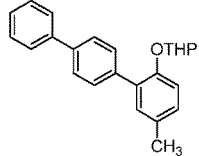
Figure 2:
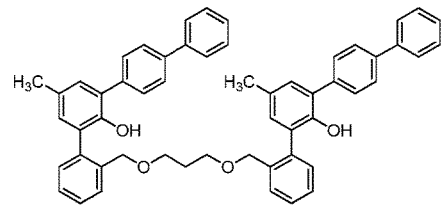
Figure 2:
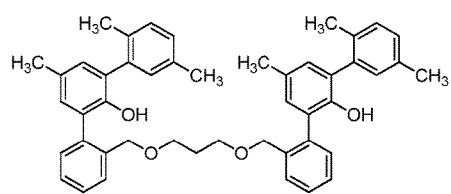
Figure 3:
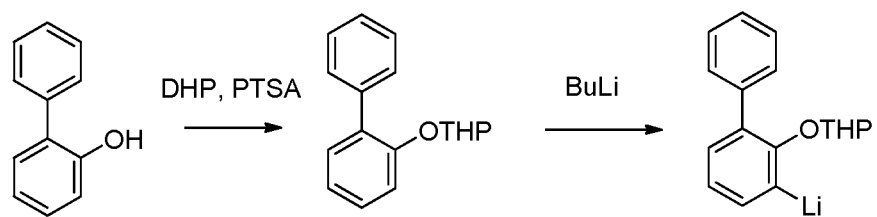
FIGS. 3 to 10 depict exemplary reaction schemes in accordance with the present disclosure.

Before the present compounds, components, compositions, and/or methods are disclosed and described, it is to be understood that unless otherwise indicated this invention is not limited to specific compounds, components, compositions, reactants, reaction conditions, ligands, transition metal compounds, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an" and "the" include plural referents unless otherwise specified. Thus, for example, reference to "a halogen atom" as in a moiety "substituted with a halogen atom" includes more than one halogen atom, such that the moiety may be substituted with two or more halogen atoms, reference to "a substituent" includes one or more substituents, reference to "a ligand" includes one or more ligands, and the like.

As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form noted with Roman numerals (also appearing in the same), or unless otherwise noted.

General Definitions

As used herein, a "catalyst composition" includes one or more catalyst compounds utilized to polymerize olefins and one or more activators or, alternatively, one or more cocatalysts. The catalyst composition may include any suitable number of catalyst compounds in any combination as described herein, as well as any activator or cocatalyst in any combination as described herein.

As used herein, a "supported catalyst composition" includes one or more catalyst compounds utilized to polymerize olefins and one or more activators or, alternatively, one or more cocatalysts, and one or more supports. The supported catalyst composition may include any suitable number of catalyst compounds in any combination as described herein, as well as any activator or cocatalyst in any combination as described herein. A "supported catalyst composition" may also contain one or more additional components known in the art to reduce or eliminate reactor fouling such as continuity additives.

As used herein, a "catalyst compound" may include any compound that, when activated, is capable of catalyzing the polymerization or oligomerization of olefins, wherein the catalyst compound comprises at least one Group 3 to 12 atom, and optionally at least one leaving group bound thereto.

The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, iso-butyl, t-butyl, octyl, decyl, and the like, as well as cycloalkyl groups such as cyclopentyl, cyclohexyl and the like. Generally, although again not necessarily, alkyl groups herein may contain 1 to about 12 carbon atoms. The term "lower alkyl" intends an alkyl group of one to six carbon atoms, specifically one to four carbon atoms. "Substituted alkyl" refers to alkyl substituted with one or more substituent groups (e.g., benzyl or chloromethyl), and the terms "heteroatom-containing alkyl" and "heteroalkyl" refer to alkyl in which at least one carbon atom is replaced with a heteroatom (e.g., $-CH_2OCH_3$ is an example of a heteroalkyl).

The term "alkenyl" as used herein refers to a branched or unbranched hydrocarbon group typically although not necessarily containing 2 to about 50 carbon atoms and at least one double bond, such as ethenyl, n-propenyl, iso-propenyl, n-butenyl, iso-butenyl, octenyl, decenyl, and the like. Generally, although again not necessarily, alkenyl groups herein contain 2 to about 12 carbon atoms. The term "lower alkenyl" refers to an alkenyl group of two to six carbon atoms, specifically two to four carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 50 carbon atoms and at least one triple bond, such as ethynyl, n-propynyl, iso-propynyl, n-butynyl, isobutynyl, octynyl, decynyl, and the like. Generally, although again not necessarily, alkynyl groups herein may have 2 to about 12 carbon atoms. The term "lower alkynyl" refers to an alkynyl group of two to six carbon atoms, specifically three or four carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group refers to an alkoxy group having one to six, more specifically one to four, carbon atoms. The term "aryloxy" is used in a similar fashion, with aryl as defined below. The term "hydroxy" refers to —OH.

Similarly, the term "alkylthio" as used herein intends an alkyl group bound through a single, terminal thioether linkage; that is, an "alkylthio" group may be represented as —S-alkyl where alkyl is as defined above. A "lower alkyl thio" group refers to an alkyl thio group having one to six, more specifically one to four, carbon atoms. The term "arylthio" is used similarly, with aryl as defined below. The term "thioxy" refers to —SH.

The term "allenyl" is used herein in the conventional sense to refer to a molecular segment having the structure $-CH=C=CH_2$. An "allenyl" group may be unsubstituted or substituted with one or more non-hydrogen substituents.

The term "aryl" as used herein, and unless otherwise specified, refers to an aromatic substituent containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, phenanthrenyl, and the like. The aryl substituents may have 1 to about 200 carbon atoms, typically 1 to about 50 carbon atoms, and specifically 1 to about 20 carbon atoms. "Substituted aryl" refers to an aryl moiety substituted with one or more substituent groups, (e.g., tolyl, mesityl and perfluorophenyl) and the terms "heteroatom-containing aryl" and "heteroaryl" refer to aryl in which at least one carbon atom is replaced with a heteroatom (e.g., rings such as thiophene, pyridine, isoxazole, pyrazole, pyrrole, furan, etc. or benzo-fused analogues of these rings are included in the term "heteroaryl"). In some embodiments herein, multi-ring moieties are substituents and in such an embodiment the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl or 9-phenanthrenyl.

The term "aralkyl" refers to an alkyl group with an aryl substituent, and the term "aralkylene" refers to an alkylene group with an aryl substituent; the term "alkaryl" refers to an aryl group that has an alkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur, phosphorus, boron or silicon. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. When the term "heteroatom-containing" appears prior to a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

"Hydrocarbyl" refers to hydrocarbyl radicals containing 1 to about 50 carbon atoms, specifically 1 to about 24 carbon atoms, most specifically 1 to about 16 carbon atoms, including branched or unbranched, saturated or unsaturated species, such as alkyl groups, alkenyl groups, aryl groups, and the like. The term "lower hydrocarbyl" refers to a hydrocarbyl group of one to six carbon atoms, specifically one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom.

By "substituted" as in "substituted hydrocarbyl," "substituted aryl," "substituted alkyl," "substituted alkenyl" and the like, as alluded to in some of the aforementioned definitions, is meant that in the hydrocarbyl, hydrocarbylene, alkyl, alkenyl, aryl or other moiety, at least one hydrogen atom bound to a carbon atom is replaced with one or more substituents that are functional groups such as hydroxyl, alkoxy, alkylthio, phosphino, amino, halo, silyl, and the like. When the term "substituted" appears prior to a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

By "divalent" as in "divalent hydrocarbyl", "divalent alkyl", "divalent aryl" and the like, is meant that the hydrocarbyl, alkyl, aryl or other moiety is bonded at two points to atoms, molecules or moieties with the two bonding points being covalent bonds. The term "aromatic" is used in its usual sense, including unsaturation that is essentially delocalized across multiple bonds, such as around a ring.

As used herein the term "silyl" refers to the —SiZ$^1$Z$^2$Z$^3$ radical, where each of Z$^1$, Z$^2$, and Z$^3$ is independently selected from the group consisting of hydride and optionally substituted alkyl, alkenyl, alkynyl, heteroatom-containing alkyl, heteroatom-containing alkenyl, heteroatom-containing alkynyl, aryl, heteroaryl, alkoxy, aryloxy, amino, silyl and combinations thereof.

As used herein the term "boryl" refers to the —BZ$^1$Z$^2$ group, where each of Z$^1$ and Z$^2$ is as defined above.

As used herein, the term "phosphino" refers to the group —PZ$^1$Z$^2$, where each of Z$^1$ and Z$^2$ is as defined above. As used herein, the term "phosphine" refers to the group PZ$^1$Z$^2$Z$^3$, where each of Z$^1$, Z$^2$ and Z$^3$ is as defined above. The term "amino" is used herein to refer to the group —NZ$^1$Z$^2$, where each of Z$^1$ and Z$^2$ is as defined above. The term "amine" is used herein to refer to the group NZ$^1$Z$^2$Z$^3$, where each of Z$^1$, Z$^2$ and Z$^3$ is as defined above.

The term "saturated" refers to lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, acetylide, oxazolinyl, cyclohexenyl, acetyl and the like.

Other abbreviations used herein include: "iPr" to refer to isopropyl; "tBu" to refer to tertbutyl; "Me" to refer to methyl; "Et" to refer to ethyl; and "Ph" refers to phenyl.

Specific ligands disclosed herein include:

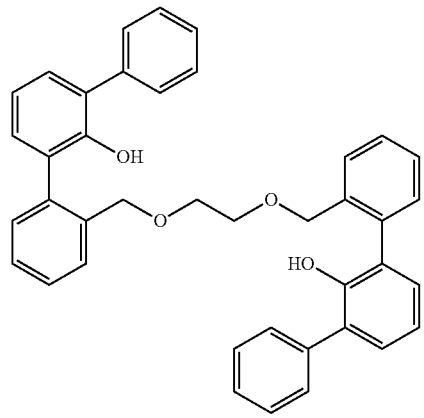

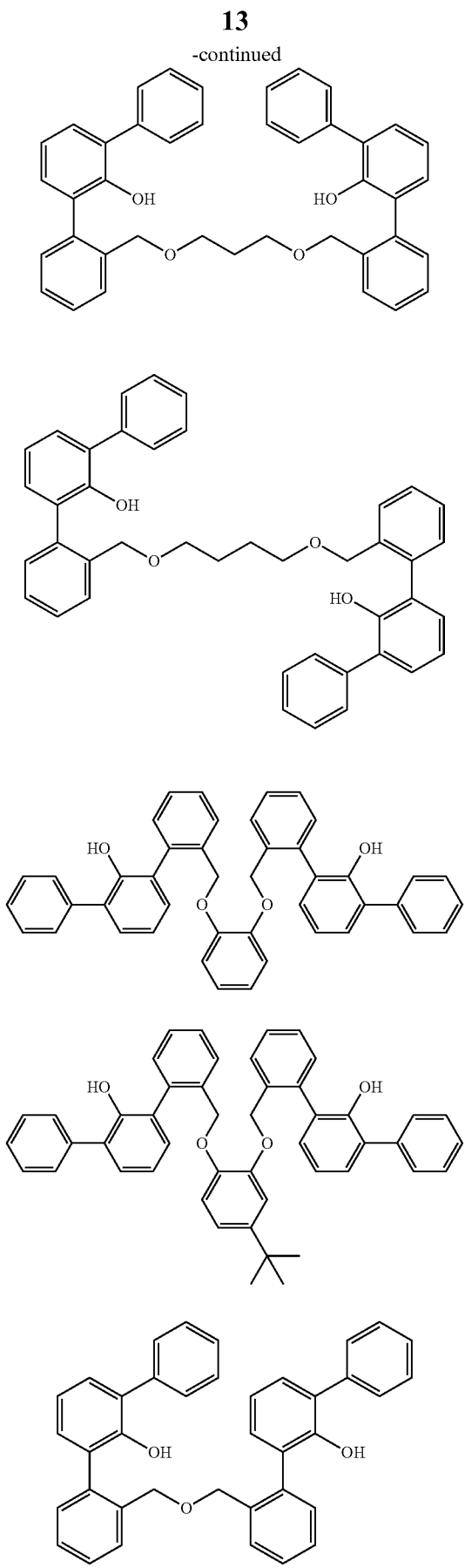

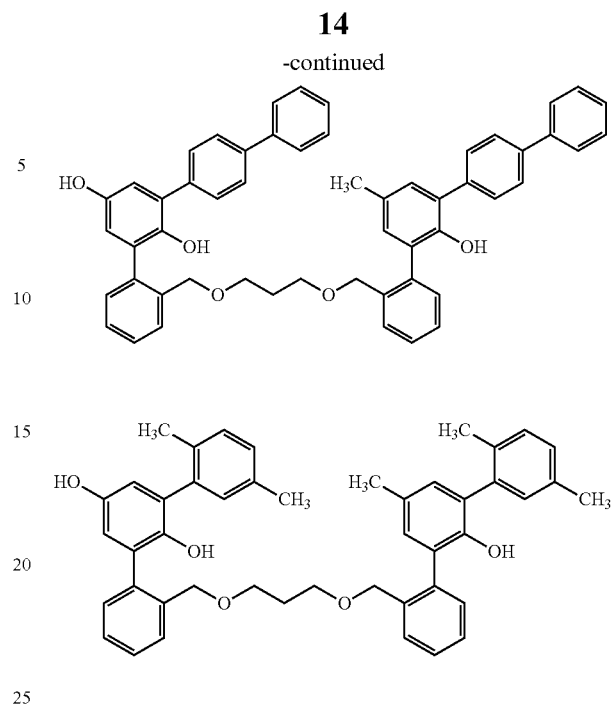

Ligand Synthesis

The ligands disclosed herein may be prepared by a variety of methods. In general the ligands may be prepared by employing ortho directed lithiations of the aromatic rings of protected phenols and aryl coupling reactions. The methods may comprise Negishi coupling or Suzuki coupling or both.

The following schemes illustrate general methods for the preparation of the ligands. In Scheme 1 an optionally substituted phenol may be protected and then selectively ortho lithiated.

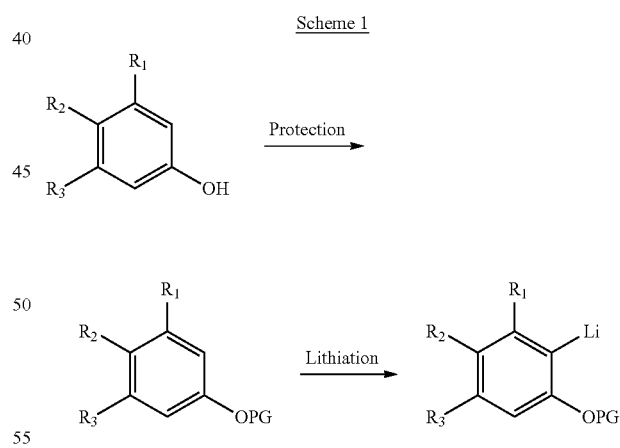

In Scheme 2 protection and lithiation of a different optionally substituted phenol is illustrated.

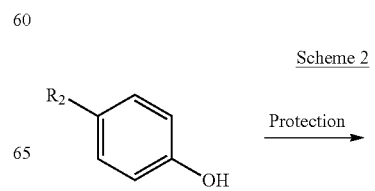

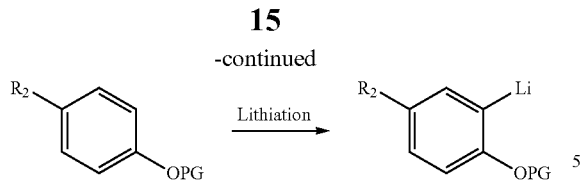
In Scheme 3 a lithiated protected phenol may be coupled via a Negishi reaction with a bridged diaryl halide.
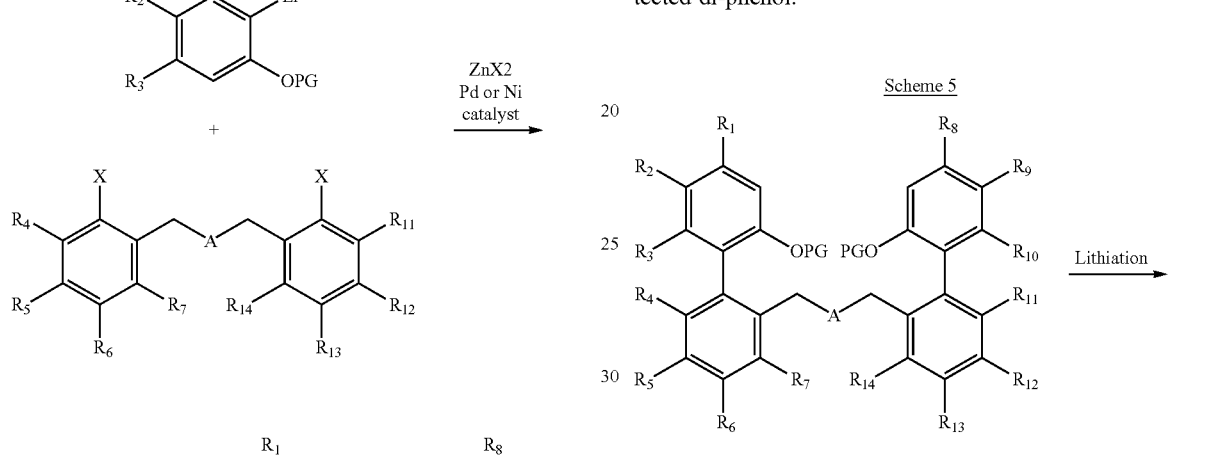
In Scheme 4 coupling is illustrated with a different optionally substituted phenol.
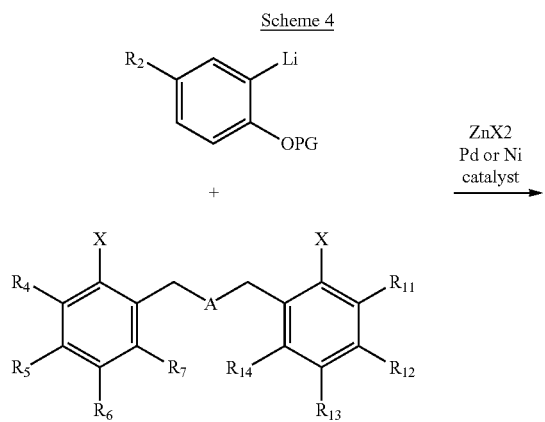
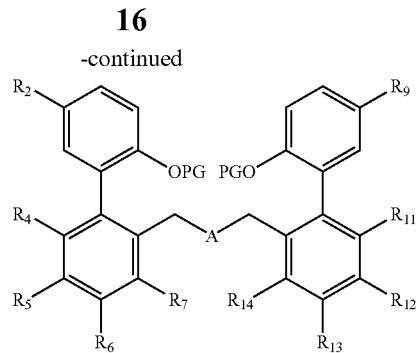
Scheme 5 illustrates di-ortho lithiation of a bridged protected di-phenol.
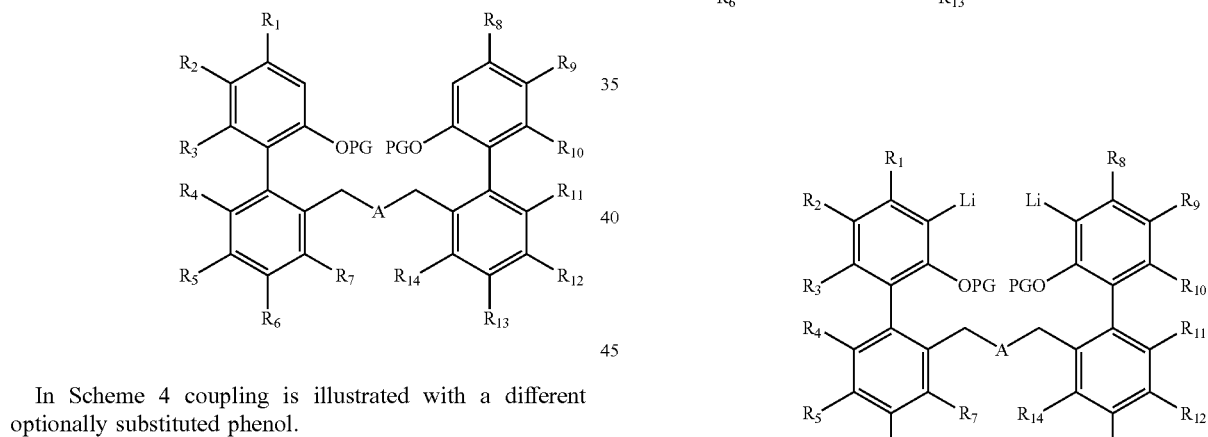
Scheme 6 illustrates a further di-ortho lithiation.
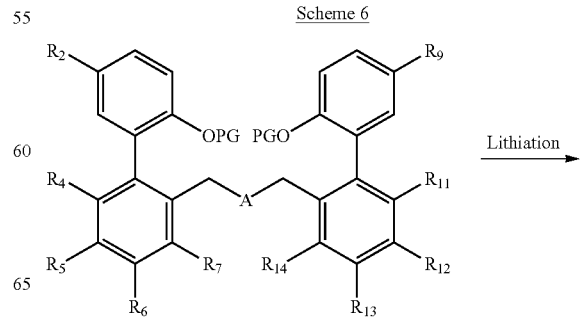

Scheme 7 illustrates arylation via Negishi coupling.
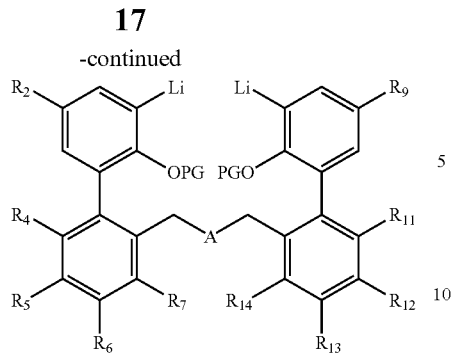
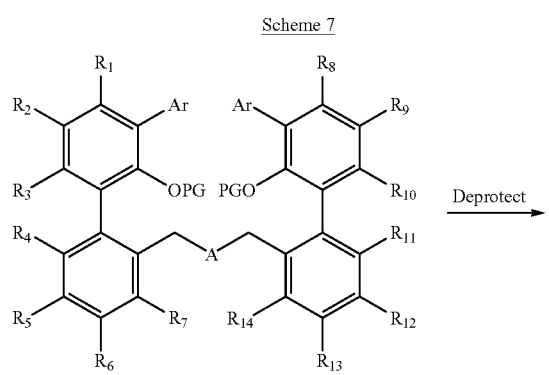
Scheme 8 illustrates arylation via Negishi coupling.
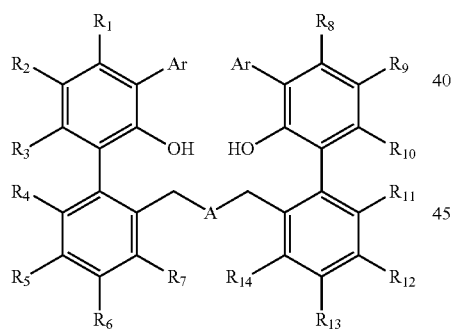
Scheme 9 illustrates deprotection.
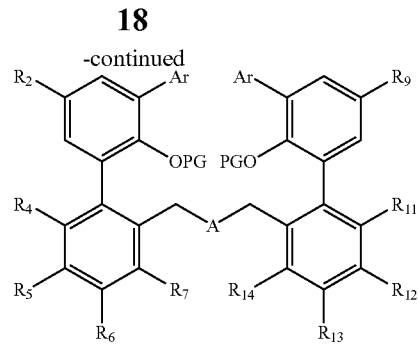
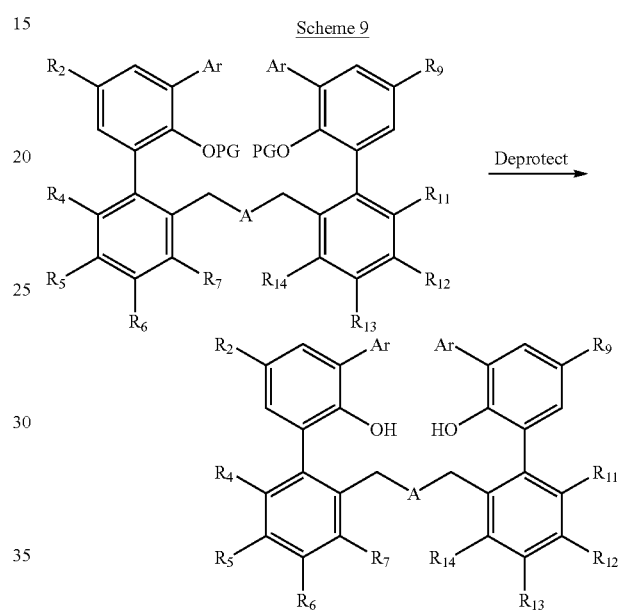
Scheme 10 illustrates deprotection.
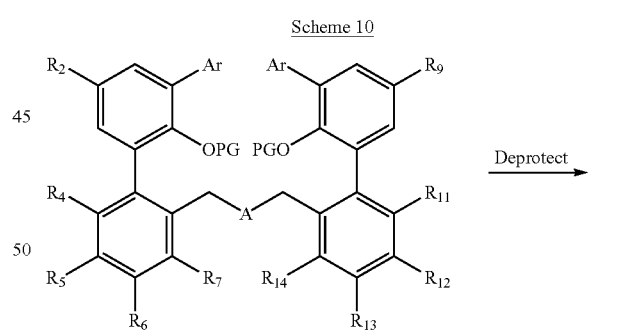
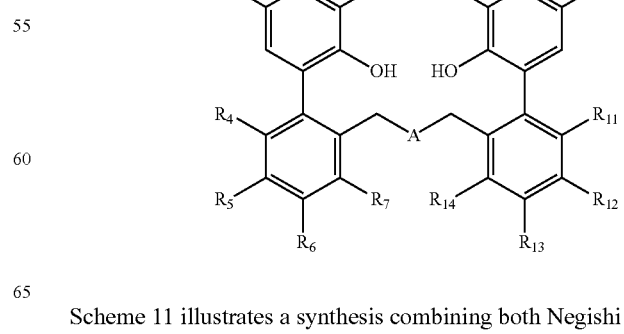
Scheme 11 illustrates a synthesis combining both Negishi and Suzuki coupling.

Scheme 11

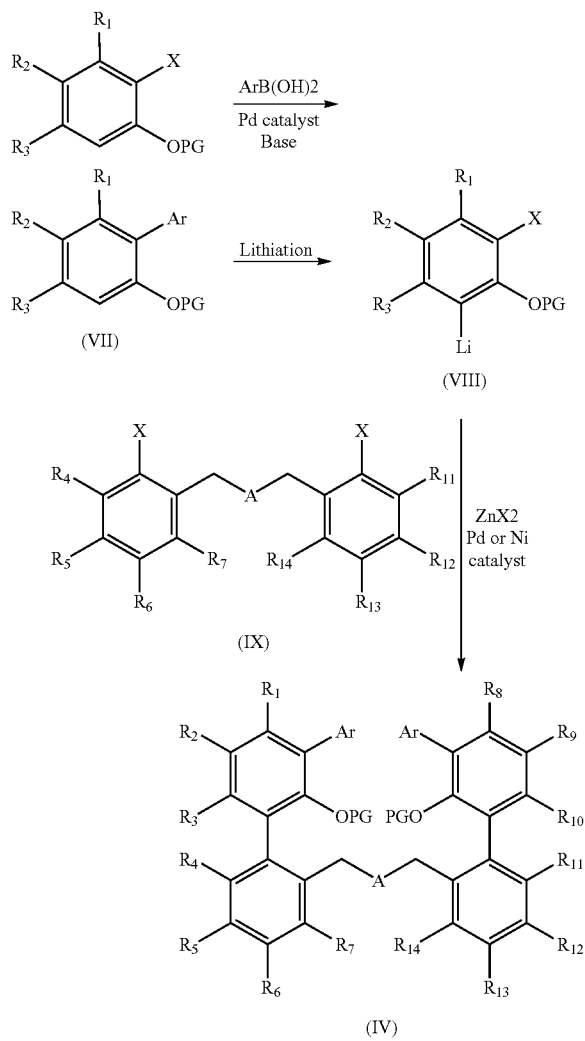

Scheme 12 illustrates a general method of synthesizing ether bridged biphenyl phenols.

Scheme 12

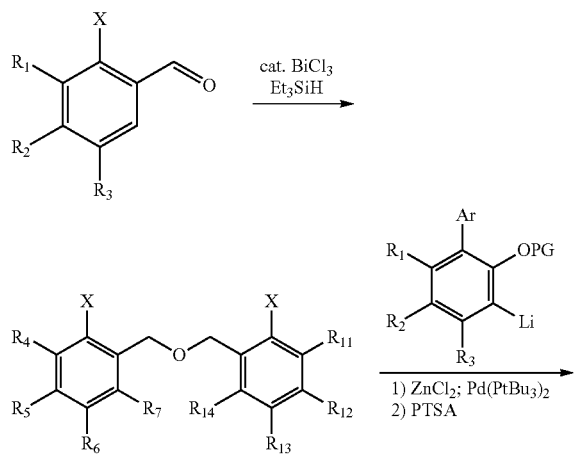

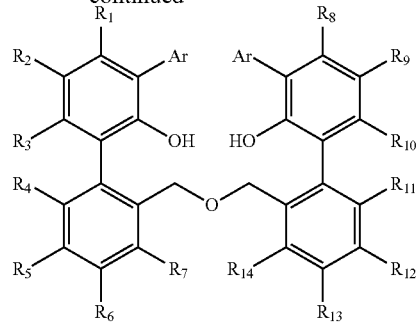

wherein in any one of the above methods each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydride, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is O, S, $NR^a$ and $PR^a$ wherein $R^a$ is optionally substituted hydrocarbyl, or A is —Y-E-Y'— wherein E is a bridging group having from one to 50 non-hydrogen atoms; Y and Y' are independently selected from O, S, $NR^a$ and $PR^a$ wherein $R^a$ is optionally substituted hydrocarbyl; Ar is optionally substituted aryl or heteroaryl; X is halide; PG is a protecting group.

In any one of the above methods each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ may be independently selected from the group consisting of hydride and optionally substituted aryl and hetroaryl.

In any of the above methods Y and Y' may be O.

In any of the above methods A may be selected from the group consisting of optionally substituted divalent alkyl, alkenyl, alkynyl, heteroalkyl, heteroalkenyl, heteroalkynyl, aryl, heteroaryl and silyl.

In any of the above methods lithiation may be performed with an alkyl or aryl lithium compound. For example. t-BuLi, lithium bis(trimethylsilyl)amide (LHMDS), lithium diisopropylamide, and lithium tetramethylpiperidide.

In any of the above methods the palladium catalyst may comprise a palladium phosphine compound, for example, bis(tri-tert-butylphosphine)palladium ($Pd(PPh_3)_4$), tetrakis(triphenylphosphine)palladium(0) ($Pd(dppe)_2$), bis[1,2-bis(diphenylphosphino)ethane]palladium(0) (Pd(dppf)), 1,1'-bis(diphenylphosphino)ferrocene palladium, and (2,2'-bis(diphenylphosphino)-1,1'-binaphthyl palladium (Pd (BINAP).

In any of the above methods the palladium catalyst may comprise a palladium compound and one or more phosphines. For example, tris(dibenzylideneacetone)dipalladium (0) ($Pd_2(dba)_3$) and $Pd(OAc)_2$ and one or more phosphine compounds.

In any of the above methods the zinc halide may be zinc (II) chloride.

In any one of the aforementioned embodiments deprotection may comprise treatment with acid. The acid may be any protic acid. Exemplary acids include hydrochloric acid or p-toluene sulfonic acid.

An advantage of the hereinbefore disclosed methods is the use of direct and selective ortho lithiation of the aromatic ring of a protected phenol. This obviates the need to perform multiple halogenations of the phenol rings prior to lithiation.

Figure 4:
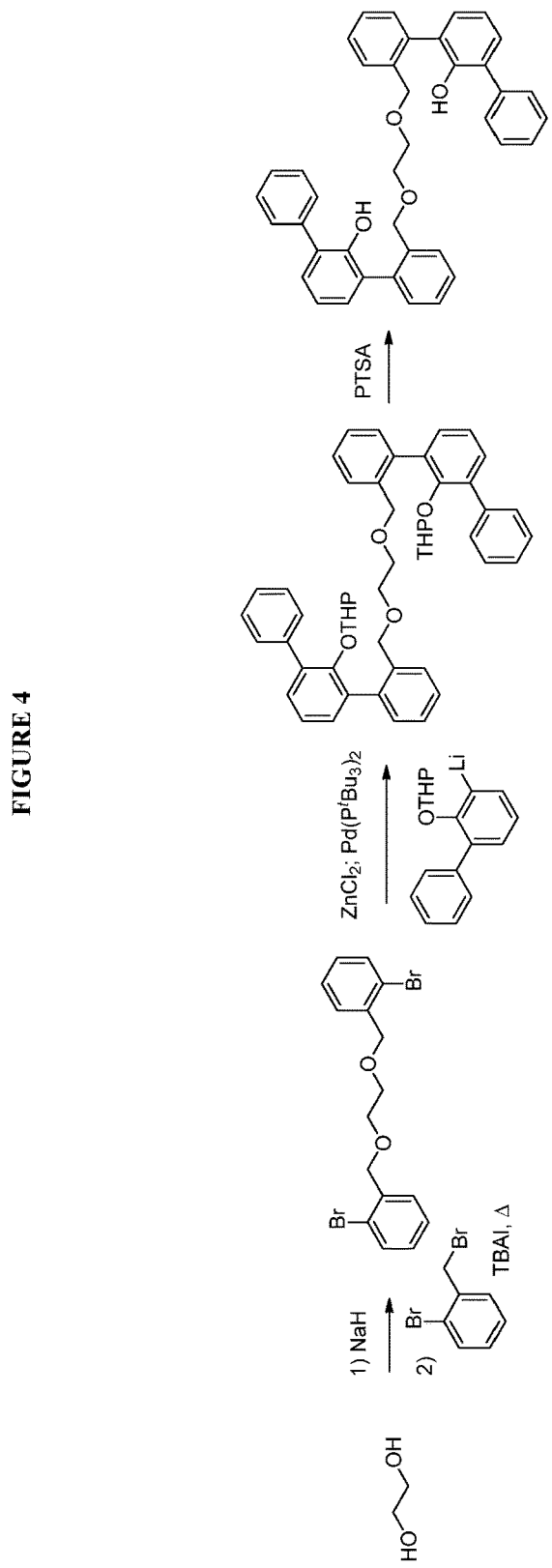
Figure 5:
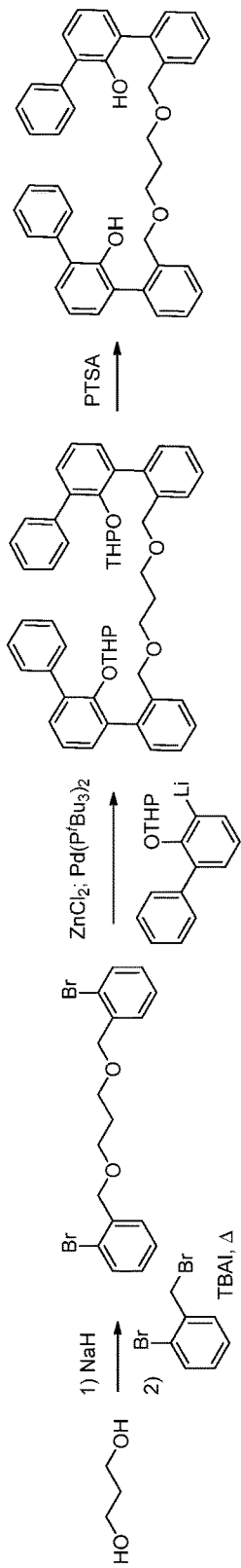
Figure 6:
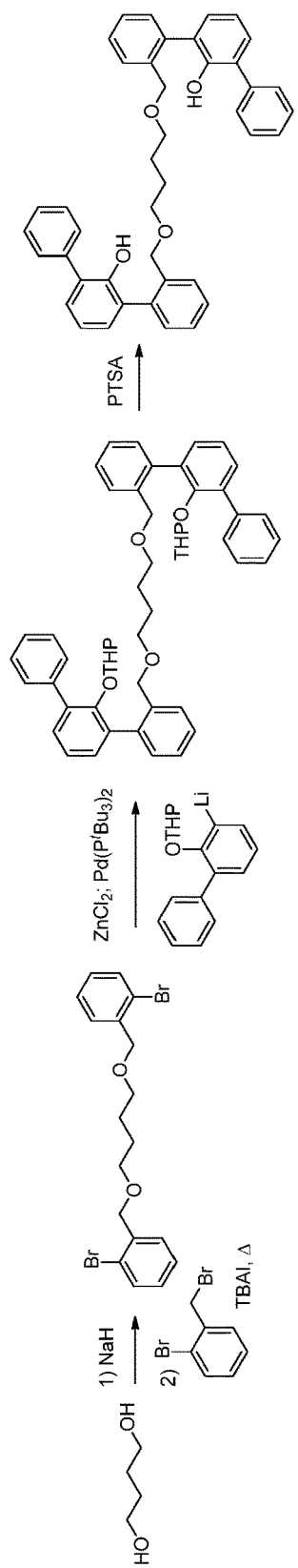
Figure 7:
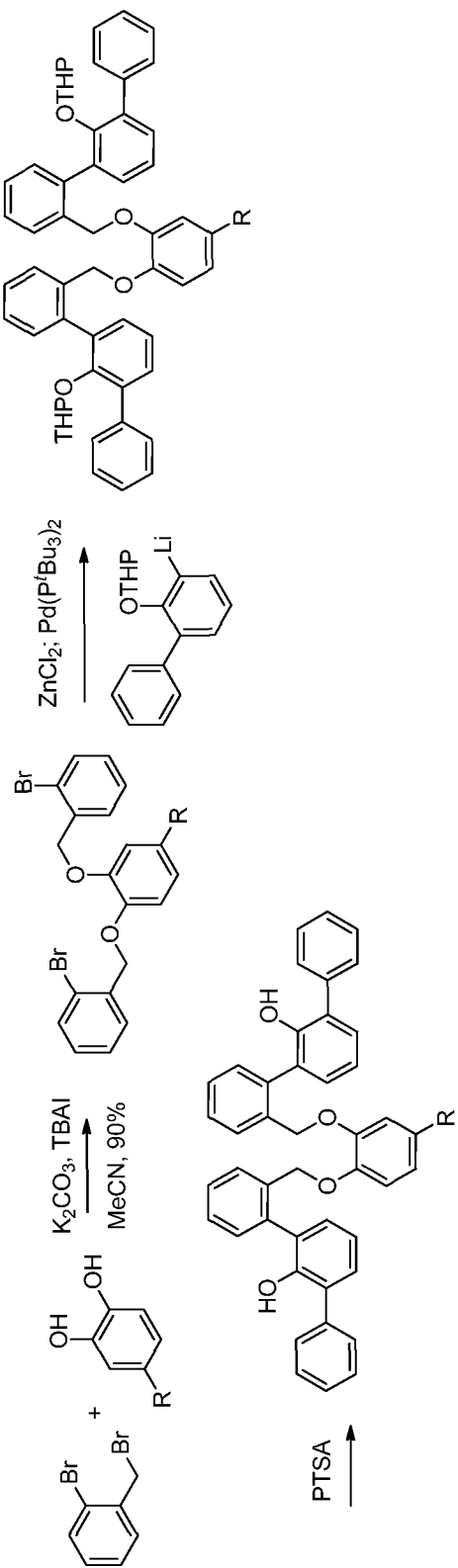
Figure 8:
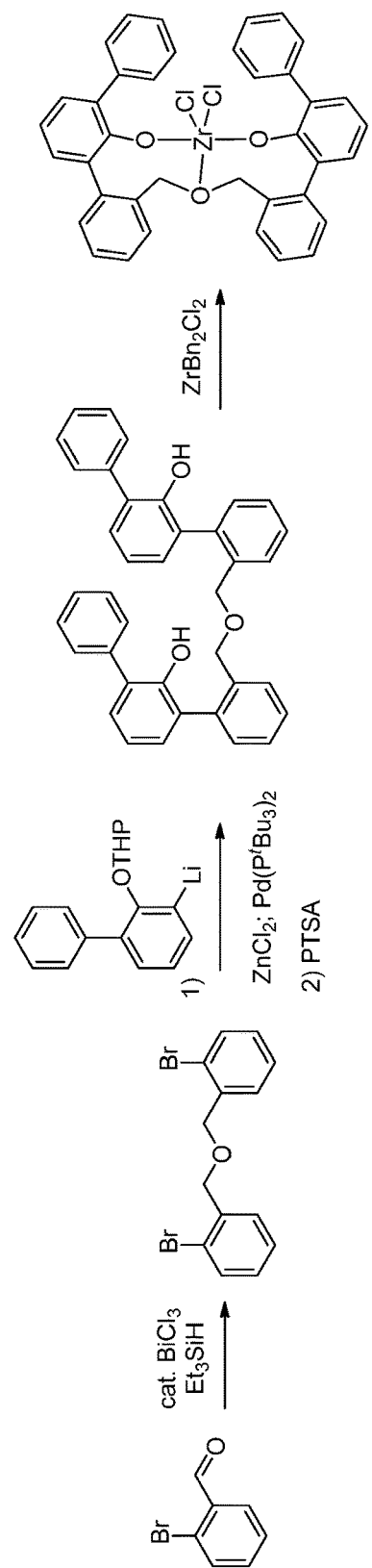
Figure 9:
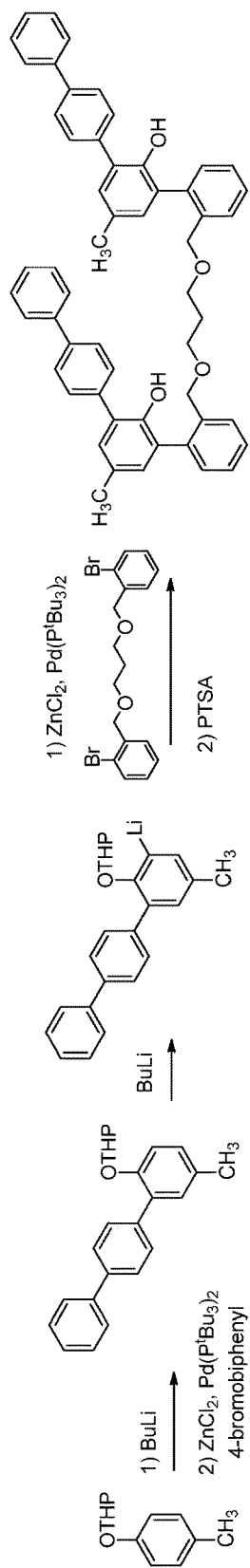
Figure 10:
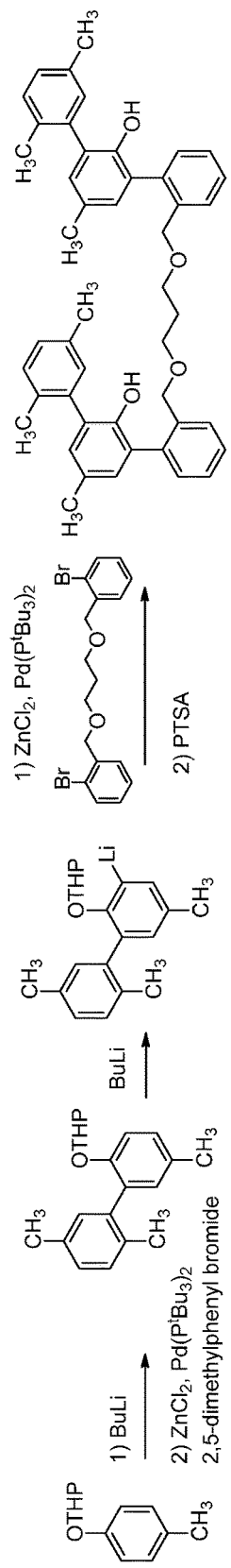

In an illustrative embodiment and referring to the structures in FIG. 1 and the reaction scheme in FIG. 4, propanediol was treated with sodium hydride and 2-bromobenzyl-bromide to yield 1,3-bis((2-bromobenzyl)oxy)propane. The phenyl phenol lithium salt was treated with zinc dichloride followed by the bisbromobenzyloxybenzene and bis(tri-tert-butylphosphine)palladium followed by deprotection with p-TSA to yield 2,2'''-((propane-1,3-diylbisoxy)bismethylene)bis([1,1':3',1''-terphenyl]-2'-ol).

FIGS. 3 and 5 to 10 illustrate further exemplary reaction schemes.

Catalyst Compounds

The catalyst compounds may be prepared by any suitable synthesis method and the method of synthesis is not critical to the present disclosure. One useful method of preparing the catalyst compounds of the present disclosure is by reacting a suitable metal compound, for example one having a displaceable anionic ligand, with the bridged bi-aromatic ligands of this disclosure. Non-limiting examples of suitable metal compounds include organometallics, metal halids, sulfonates, carboxylates, phosphates, organoborates (including fluoro-containing and other subclasses), acetonacetonates, sulfides, sulfates, tetrafluoroborates, nitrates, perchlorates, phenoxides, alkoxides, silicates, arsenates, borohydrides, naphthenates, cyclooctadienes, diene conjugated complexes, thiocynates, cyanates, and the metal cyanides. The metal compound may be an organometallic or metal halide. The metal compound may be an organometallic.

The metal of the organometallic compound may be selected from Groups 1 to 16, or a transition metal selected from Groups 3 to 13 elements and Lanthanide series elements. The metal may be selected from Groups 3 to 7 elements. The metal may be a Group 4 metal, titanium, zirconium or hafnium.

The metal compound can, for example, be a metal hydrocarbyl such as: a metal alkyl, a metal aryl, a metal arylalkyl; a metal silylalkyl; a metal diene, a metal amide; or a metal phosphide. The metal compound may be a zirconium or hafnium hydrocarbyl. The transition metal compound may be a zirconium arylalkyl.

Examples of useful and preferred metal compounds include:

(i) tetramethylzirconium, tetraethylzirconium, zirconiumdichloride ($\eta^4$-1,4-diphenyl-1,3-butadiene), bis (triethylphosphine) and zirconiumdichloride ($\eta^4$-1,4-diphenyl-1,3-butadiene) bis (tri-n-propylphosphine), tetrakis[trimethylsilylmethyl]zirconium, tetrakis[dimethylamino]zirconium, dichlorodibenzylzirconium, chlorotribenzylzirconium, trichlorobenzylzirconium, bis[dimethylamino]bis[benzyl]zirconium, and tetrabenzylzirconium;

(ii) tetramethyltitanium, tetraethyltitanium, titaniumdichloride ($\eta^4$-1,4-diphenyl-1,3-butadiene), bis (triethylphosphine) and titaniumdichloride ($\eta^4$-1,4-diphenyl-1,3-butadiene) bis (tri-n-propylphosphine), tetrakis[trimethylsilylmethyl] titanium, tetrakis[dimethylamino] titanium, dichlorodibenzyltitanium, chlorotribenzyltitanium, trichlorobenzyltitanium, bis[dimethylamino]bis[benzyl]titanium, and tetrabenzyltitanium; and (iii) tetramethylhafnium, tetraethylhafnium, hafniumdichloride ($\eta^4$-1,4-diphenyl-1,3-butadiene), bis (triethylphosphine) and hafniumdichloride ($\eta^4$-1,4-diphenyl-1,3-butadiene) bis (tri-n-propylphosphine), tetrakis[trimethylsilylmethyl]hafnium, tetrakis[dimethylamino] hafnium, dichlorodibenzylhafnium, chlorotribenzylhafnium, trichlorobenzylhafnium, bis[dimethylamino]bis[benzyl]hafnium, and tetrabenzylhafnium.

Exemplary reactions are shown below:

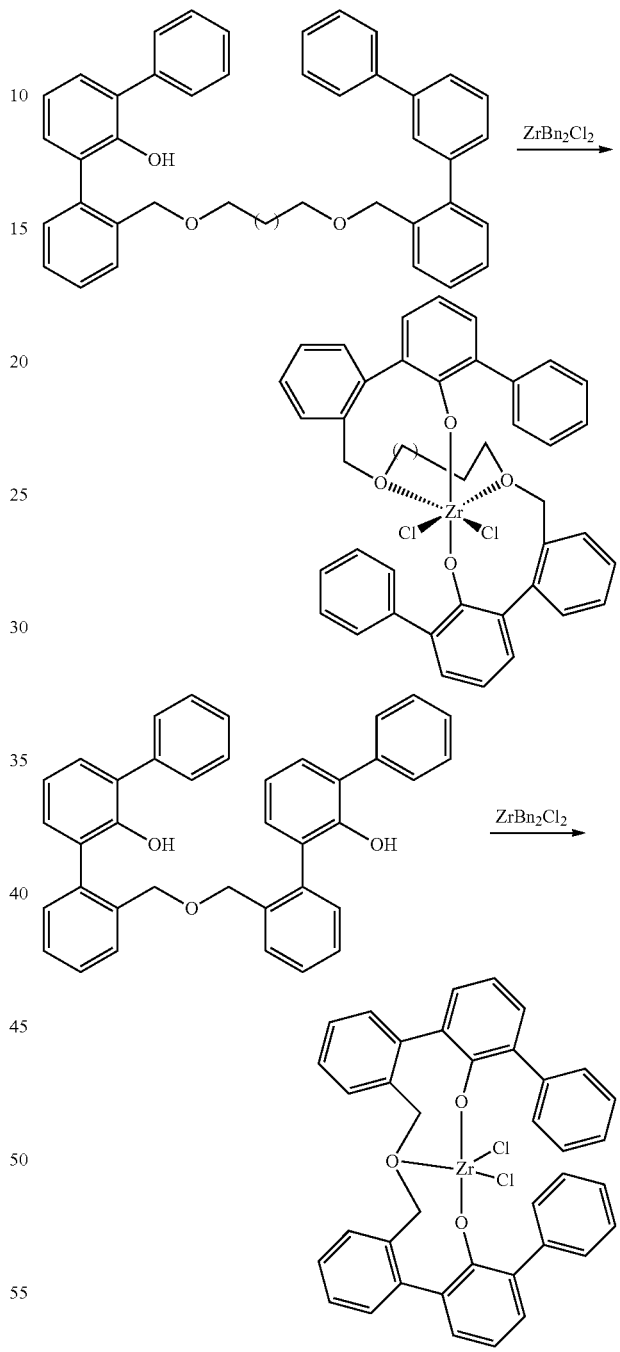

Catalyst and Supported Catalyst Compositions

The catalyst compositions disclosed herein may comprise one or more activators as disclosed herein and one or more catalyst compounds as disclosed herein.

The supported catalyst compositions as disclosed herein may comprise one or more supports as disclosed herein, one or more activators as disclosed herein, and one or more catalyst compounds as disclosed herein.

The catalyst compositions and supported catalyst compositions may comprise one or more of the catalyst compounds as hereinbefore disclosed along with another catalyst compound, such as a metallocene catalyst compound or a Group V atom containing catalyst compound. Suitable other catalyst compounds include, but are not limited to:

(pentamethylcyclopentadienyl)(propylcyclopentadienyl) $MX_2$,
(tetramethylcyclopentadienyl)(propylcyclopentadienyl) $MX_2$,
(tetramethylcyclopentadienyl)(butylcyclopentadienyl) $MX_2$,
$Me_2Si(indenyl)_2MX_2$,
$Me_2Si(tetrahydroindenyl)_2MX_2$,
(n-propyl cyclopentadienyl)$_2MX_2$,
(n-butyl cyclopentadienyl)$_2MX_2$,
(1-methyl, 3-butyl cyclopentadienyl)$_2MX_2$,
$HN(CH_2CH_2N(2,4,6-Me_3phenyl))_2MX_2$,
$HN(CH_2CH_2N(2,3,4,5,6-Me_5phenyl))_2MX_2$,
(propyl cyclopentadienyl)(tetramethylcyclopentadienyl) $MX_2$,
(butyl cyclopentadienyl)$_2MX_2$,
(propyl cyclopentadienyl)$_2MX_2$, and mixtures thereof, wherein M is Zr or Hf, and X is selected from F, Cl, Br, I, Me, benzyl, $CH_2SiMe_3$, and $C_1$ to $C_5$ alkyls or alkenyls.

The supported catalyst composition may in the form of a substantially dry powder or be in the form of a slurry in at least one liquid vehicle. Non-limiting examples of liquid vehicles include mineral oils, aromatic hydrocarbons or aliphatic hydrocarbons.

Activator Compounds

An activator is defined in a broad sense as any combination of reagents that increases the rate at which a transition metal compound oligomerizes or polymerizes unsaturated monomers, such as olefins. The catalyst compounds may be activated for oligomerization and/or polymerization catalysis in any manner sufficient to allow coordination or cationic oligomerization and/or polymerization.

Additionally, the activator may be a Lewis-base, such as for example, diethyl ether, dimethyl ether, ethanol, or methanol. Other activators that may be used include those described in WO 98/07515 such as tris (2,2',2"-nonafluoro-biphenyl) fluoroaluminate.

Combinations of activators may be used. For example, alumoxanes and ionizing activators may be used in combinations, see for example, EP-B1 0 573 120, WO 94/07928 and WO 95/14044 and U.S. Pat. Nos. 5,153,157 and 5,453,410. WO 98/09996 describes activating metallocene catalyst compounds with perchlorates, periodates and iodates including their hydrates. WO 98/30602 and WO 98/30603 describe the use of lithium (2,2'-bisphenyl-ditrimethylsilicate). 4THF as an activator for a metallocene catalyst compound. WO 99/18135 describes the use of organo-boron-aluminum activators. EP-B1-0 781 299 describes using a silylium salt in combination with a non-coordinating compatible anion. WO 2007/024773 suggests the use of activator-supports which may comprise a chemically-treated solid oxide, clay mineral, silicate mineral, or any combination thereof. Also, methods of activation such as using radiation (see EP-B1-0 615 981), electro-chemical oxidation, and the like are also contemplated as activating methods for the purposes of rendering the neutral metallocene catalyst compound or precursor to a metallocene cation capable of polymerizing olefins. Other activators or methods for activating a metallocene catalyst compound are described in, for example, U.S. Pat. Nos. 5,849,852, 5,859,653 and 5,869,723 and PCT WO 98/32775.

Alumoxanes may also be utilized as an activator in the catalyst composition. Alumoxanes are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is a halide. Mixtures of different alumoxanes and modified alumoxanes may also be used. For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1, EP 0 516 476 A, EP 0 594 218 A1 and WO 94/10180.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in, for example, U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, WO 94/10180 and WO 99/15534. A visually clear methylalumoxane may be used. A cloudy or gelled alumoxane can be filtered to produce a clear solution or clear alumoxane can be decanted from the cloudy solution. Another alumoxane is a modified methyl alumoxane (MMAO) cocatalyst type 3A (commercially available from Akzo Chemicals, Inc. under the trade name Modified Methylalumoxane type 3A, disclosed in U.S. Pat. No. 5,041,584).

An ionizing or stoichiometric activator, neutral or ionic, such as tri (n-butyl) ammonium tetrakis (pentafluorophenyl) boron, a trisperfluorophenyl boron metalloid precursor or a trisperfluoronapthyl boron metalloid precursor, polyhalogenated heteroborane anions (see, for example, WO 98/43983), boric acid (see, for example, U.S. Pat. No. 5,942,459) or combinations thereof, may also be used. The neutral or ionic activators may be used alone or in combination with alumoxane or modified alumoxane activators.

Examples of neutral stoichiometric activators may include tri-substituted boron, tellurium, aluminum, gallium and indium or mixtures thereof. The three substituent groups may be each independently selected from the group of alkyls, alkenyls, halogen, substituted alkyls, aryls, arylhalides, alkoxy and halides. The three substituent groups may be independently selected from the group of halogen, mono or multicyclic (including halosubstituted) aryls, alkyls, and alkenyl compounds and mixtures thereof; or alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). Alternatively, the three groups are alkyls having 1 to 4 carbon groups, phenyl, napthyl or mixtures thereof. The three groups may be halogenated, for example fluorinated, aryl groups. In yet other illustrative examples, the neutral stoichiometric activator is trisperfluorophenyl boron or trisperfluoronapthyl boron.

Ionic stoichiometric activator compounds may contain an active proton, or some other cation associated with, but not coordinated to, or only loosely coordinated to, the remaining ion of the ionizing compound. Such compounds and the like are described in, for example, European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124.

Supports

The above described catalyst compounds may be combined with one or more supports using one of the support methods well known in the art or as described below. For example, the catalyst compound may be used in a supported form, such as, deposited on, contacted with, or incorporated within, adsorbed or absorbed in, or on the support.

As used herein, the term "support" refers to compounds comprising Group 2, 3, 4, 5, 13 and 14 oxides and chlorides. Suitable supports include, for example, silica, magnesia, titania, zirconia, montmorillonite, phyllosilicate, alumina, silica-alumina, silica-chromium, silica-titania, magnesium chloride, graphite, magnesia, titania, zirconia, montmorillonite, phyllosilicate, and the like.

The support may possess an average particle size in the range of from about 0.1 to about 500 µm, or from about 1 to about 200 µm, or from about 1 to about 50 µm, or from about 5 to about 50 µm.

The support may have an average pore size in the range of from about 10 to about 1000 Å, or about 50 to about 500 Å, or 75 to about 350 Å.

The support may have a surface area in the range of from about 10 to about 700 m$^2$/g, or from about 50 to about 500 m$^2$/g, or from about 100 to about 400 m$^2$/g.

The support may have a pore volume in the range of from about 0.1 to about 4.0 cc/g, or from about 0.5 to about 3.5 cc/g, or from about 0.8 to about 3.0 cc/g.

The support, such as an inorganic oxide, may have a surface area in the range of from about 10 to about 700 m$^2$/g, a pore volume in the range of from about 0.1 to about 4.0 cc/g, and an average particle size in the range of from about 1 to about 500 µm. Alternatively, the support may have a surface area in the range of from about 50 to about 500 m$^2$/g, a pore volume of from about 0.5 to about 3.5 cc/g, and an average particle size of from about 10 to about 200 µm. The surface area of the support may be in the range from about 100 to about 400 m$^2$/g, a pore volume of from about 0.8 to about 3.0 cc/g and an average particle size of from about 5 to about 100 µm.

The catalyst compounds may be supported on the same or separate supports together with an activator, or the activator may be used in an unsupported form, or may be deposited on a support different from the supported catalyst compound.

There are various other methods in the art for supporting a polymerization catalyst compound. For example, the catalyst compound may contain a polymer bound ligand as described in, for example, U.S. Pat. Nos. 5,473,202 and 5,770,755; the catalyst may be spray dried as described in, for example, U.S. Pat. No. 5,648,310; the support used with the catalyst may be functionalized as described in European publication EP-A-0 802 203, or at least one substituent or leaving group is selected as described in U.S. Pat. No. 5,688,880.

Polymerization Processes

Polymerization processes may include solution, gas phase, slurry phase and a high pressure process or a combination thereof. In illustrative embodiments, a gas phase or slurry phase polymerization of one or more olefins at least one of which is ethylene or propylene is provided. Optionally, the reactor is a gas phase fluidized bed polymerization reactor.

The catalyst compositions or supported catalyst compositions as hereinbefore described are suitable for use in any prepolymerization and/or polymerization process over a wide range of temperatures and pressures. The temperatures may be in the range of from −60° C. to about 280° C., from 50° C. to about 200° C.; from 60° C. to 120° C. from 70° C. to 100° C. or from 80° C. to 95° C.

The present process may be directed toward a solution, high pressure, slurry or gas phase polymerization process of one or more olefin monomers having from 2 to 30 carbon atoms, preferably 2 to 12 carbon atoms, and more preferably 2 to 8 carbon atoms. The process is particularly well suited to the polymerization of two or more olefins or comonomers such as ethylene, propylene, 1-butene, 1-pentene, 4-methyl-1-pentene, 1-hexene, 1-octene 1-decene or the like.

Other olefins useful in the present process include ethylenically unsaturated monomers, diolefins having 4 to 18 carbon atoms, conjugated or nonconjugated dienes, polyenes, vinyl monomers and cyclic olefins. Useful monomers may include, but are not limited to, norbornene, norbornadiene, isobutylene, isoprene, vinylbenzocyclobutane, styrenes, alkyl substituted styrene, ethylidene norbornene, dicyclopentadiene and cyclopentene. In an illustrative embodiment of the present process, a copolymer of ethylene is produced, where with ethylene, a comonomer having at least one alpha-olefin having from 4 to 15 carbon atoms, preferably from 4 to 12 carbon atoms, and most preferably from 4 to 8 carbon atoms, is polymerized in a gas phase process. In another embodiment of the present process, ethylene or propylene is polymerized with at least two different comonomers, optionally one of which may be a diene, to form a terpolymer.

The present process may be directed to a polymerization process, particularly a gas phase or slurry phase process, for polymerizing propylene alone or with one or more other monomers including ethylene, and/or other olefins having from 4 to 12 carbon atoms. The polymerization process may comprise contacting ethylene and optionally an alpha-olefin with one or more of the catalyst compositions or supported catalyst compositions as hereinbefore described in a reactor under polymerization conditions to produce the ethylene polymer or copolymer.

Suitable gas phase polymerization processes are described in, for example, U.S. Pat. Nos. 4,543,399, 4,588,790, 5,028,670, 5,317,036, 5,352,749, 5,405,922, 5,436,304, 5,453,471, 5,462,999, 5,616,661, 5,668,228, 5,627,242, 5,665,818, and 5,677,375, and European publications EP-A-0 794 200, EP-A-0 802 202, EP-A2 0 891 990, and EP-B-634 421.

A slurry polymerization process generally uses pressures in the range of from about 1 to about 50 atmospheres and even greater and temperatures in the range of 0° C. to about 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

A preferred polymerization process is referred to as a particle form polymerization, or a slurry process where the temperature is kept below the temperature at which the polymer goes into solution. Such technique is well known in the art, and described in for instance U.S. Pat. No. 3,248,179. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484. Examples of solution processes are described in U.S. Pat. Nos. 4,271,060, 5,001,205, 5,236,998 and 5,589,555.

EXAMPLES

It is to be understood that while the present disclosure has been described in conjunction with the specific embodiments thereof, the foregoing description is intended to illustrate and not limit the scope of the disclosure. Other aspects, advantages and modifications will be apparent to those skilled in the art to which the disclosure pertains. Therefore, the following examples are put forth so as to provide those skilled in the art with a complete disclosure and description of how to make and use the disclosed compositions, and are not intended to limit the scope of the disclosure.

General:

All reagents were purchased from commercial vendors and used as received unless otherwise noted. Solvents were sparged with $N_2$ and dried over 3 Å molecular sieves. Analytical thin-layer chromatography (TLC) was performed on Selecto Plates (200 μm) precoated with a fluorescent indicator. Visualization was effected using ultraviolet light (254 nm). Flash column chromatography was carried out with Sigma Aldrich Silica gel 60 Å (70-230 Mesh) using solvent systems specified. NMR spectra were recorded on a Bruker 400 or 500 NMR with chemical shifts referenced to residual solvent peaks. Abbreviations: PTSA—para-toluenesulfonic acid; TBAI—tetrabutyl ammonium iodide.

2-([1,1'-biphenyl]-2-yloxy)tetrahydro-2H-pyran (1)

2-Phenylphenol (10 g, 58 mmol) and dihydropyran (5.5 mL, 60.2 mmol) were dissolved in methylene chloride and cooled on an ice bath. A catalytic amount (0.1 equiv.) of PTSA was added and the reaction stirred for 10 min before quenching with 4 mL of triethylamine and water. The mixture was extracted with methylene chloride and the organic portion washed with brine, dried ($MgSO_4$), filtered and concentrated. The resulting oil was vacuum distilled to remove unreacted starting material, leaving the product in 64% crude yield: $^1$H NMR (400 MHz, $CDCl_3$, δ): 1.54 (m, 6H), 3.55 (m, 1H), 3.79 (m, 1H), 5.40 (m, 1H), 7.05 (m, 1H), 7.32 (m, 6H), 7.56 (d, J=7.2 Hz, 2H).

(2-((tetrahydro-2H-pyran-2-yl)oxy)-[1,1'-biphenyl]-3-yl)lithium (2)

The above protected phenylphenol (1) (9.5 g, 37.3 mmol) was dissolved in ether and cooled to −35° C. n-Butyl lithium (15 mL of 2.5 M in hexane) was added slowly and the solution stirred for 1 h. A precipitate formed which was isolated by filtration, washed with pentane and used for subsequent reactions.

1,2-bis((2-bromobenzyl)oxy)ethane (3)

Ethylene glycol (620 mg, 10 mmol) was slowly added to sodium hydride (510 mg, 20.2 mmol) suspended in 20 mL of THF. After stirring for 20 min, 2-bromobenzylbromide (5.0 g, 20 mmol) and TBAI (approx. 100 mg) were added and the mixture heated at 50° C. until completion as monitored by TLC. The reaction was slowly quenched with water and extracted 3 times with ethyl ether. The combined organic portions were washed with 10% HCl and brine, dried ($MgSO_4$), filtered, and concentrated to give a pale yellow solid. Purification was achieved by column chromatography eluting with 30% acetone/isohexane: $R_f$=0.50 (30:70 acetone:isohexane); $^1$H NMR (400 MHz, $CDCl_3$, δ): 3.82 (s, 4H), 4.68 (s, 4H), 7.16 (m, 2H), 7.33 (m, 2H), 7.55 (m, 4H); IR ($cm^{-1}$): 3062, 2863, 1568, 1466, 1440, 1351, 1102, 1026.

2,2'''-((ethane-1,2-diylbisoxy)bismethylene)bis(([1,1':3',1''-terphenyl]-2'-ol)) (4)

The phenyl phenol lithium salt (750 mg, 2.8 mmol) was dissolved in 50 mL of THF and cooled to −70° C. Zinc dichloride (240 mg, 3.4 mmol) was added and the reaction warmed to ambient temperature for 1 h. The above bisbromobenzyloxybenzene (3) (575 mg, 1.34 mmol) and bis(tri-tert-butylphosphine)palladium (14 mg, 0.02 mmol) were added and the reaction heated at reflux overnight. After cooling, the reaction was quenched with water and extracted with 3 portions of ether. Combined organic layers were washed with brine, dried ($MgSO_4$), filtered and concentrated under reduced pressure. The crude oil was passed through a silica gel column (10% acetone/isohexane) then deprotected by heating with approx. 100 mg PTSA in a 1:1 mixture of THF/ethanol. The solvent was removed and the oil purified by column chromatography using 10% acetone/isohexane as eluent. The product was obtained as a white solid: $^1$H NMR (500 MHz, $CDCl_3$, δ): 3.49 (br s, 4H), 4.35 (m, 4H), 5.60 (br s, 2H), 7.01 (t, J=7.5 Hz, 2H), 7.10 (dd, J=1.5, 7.5 Hz, 2H), 7.34 (m, 6H), 7.39 (m, 8H), 7.49 (m, 2H), 7.56 (m, 4H); $^{13}$C NMR (125 MHz, $CDCl_3$, δ): 70.0 (2 C), 71.7 (2 C), 120 (2 C), 127.5 (2 C), 128.5 (2 C), 128.6 (2 C), 128.7 (6 C), 129.5 (2 C), 129.6 (2 C), 129.7 (6 C), 130.2 (2 C), 130.5 (2 C), 131.0 (2 C), 137.1 (2 C), 138.3 (2 C), 150.2 (2 C); IR ($cm^{-1}$): 3531, 3330, 3057, 2921, 2868, 1456, 1427, 1324, 1275, 1079, 950.

Zr complex (5):

Ligand (4) (100 mg, 172 mmol) was dissolved in 5 mL of toluene and cooled to −35° C. A solution of dibenzylzirconium(IV) chloride (67 mg, 172 mmol) in 5 mL of toluene was added to the ligand solution and the mixture was heated at 85° C. for 2 h. A white precipitate was formed, collected and washed with hexane: $^1$H NMR (400 MHz, $CD_2Cl_2$, δ): 3.60 (m, 1H), 3.84 (m, 1H), 4.25 (m, 1H), 4.45 (m, 2H), 4.71 (m, 3H), 6.89-7.49 (m, 22H), 7.74 (m, 2H).

1,3-bis((2-bromobenzyl)oxy)propane (6)

Propanediol (1.45 mL, 48 mmol) was added to a suspension of sodium hydride (1.15 g, 20 mmol) in 30 mL of THF and stirred for 15 min. 2-Bromobenzylbromide (10 g, 40 mmol) in 20 mL of THF and TBAI (approx. 100 mg) were added and the reaction heated at reflux overnight. Water was added to quench the reaction, and then the mixture was extracted 3 times with ethyl acetate. The combined organic layers were washed with brine, dried over MgSO$_4$, filtered, and concentrated under reduced pressure. The crude oil was purified by silica gel chromatography (10% acetone/hexane) giving the product in 81% yield as a pale yellow oil: $^1$H NMR (400 MHz, CDCl$_3$, δ): 2.02 (qn, J=6.4 Hz, 2H), 3.72 (t, J=6.2 Hz, 4H), 4.58 (s, 4H), 7.14 (m, 2H), 7.30 (m, 2H), 7.48 (m, 4H); NMR (125 MHz, CDCl$_3$, δ): 30.4, 68.0 (2 C), 72.4 (2 C), 122.9 (2 C), 127.6 (2 C), 129.0 (2 C), 129.2 (2 C), 132.7 (2 C), 138.1 (2 C); IR (cm$^{-1}$): 3064, 2922, 2862, 1598, 1470, 1440, 1360, 1205, 1103, 1027, 942.

2,2'''-((propane-1,3-diylbisoxy)bismethylene)bis([1, 1':3',1''-terphenyl]-2'-ol) (7)

The phenyl phenol lithium salt (1.38 g, 5.28 mmol) was dissolved in 100 mL of THF and cooled to −70° C. Zinc dichloride (870 mg, 6.33 mmol) was added and the reaction warmed to ambient temperature for 1h. The above bisbromobenzyloxybenzene (6) (1.0 g, 2.4 mmol) and bis(tri-tert-butylphosphine)palladium (25 mg, 0.05 mmol) were added and the reaction heated at reflux overnight. After cooling, the reaction was quenched with water and extracted with 3 portions of ether. Combined organic layers were washed with brine, dried (MgSO$_4$), filtered, and concentrated under reduced pressure. The crude oil was redissolved in THF/ethanol (1:1), PTSA (approx. 100 mg) was added and the solution heated at 80° C. overnight. Volatiles were removed under reduced pressure and the resulting crude oil purified by passage through a silica gel plug with 10% acetone/hexane as eluent giving the product as a solid in 25% yield: $^1$H NMR (400 MHz, CDCl$_3$, δ): 1.77 (m, 2H), 3.44 (br s, 4H), 4.31 (m, 4H), 5.79 (br s, 2H), 7.03 (t, J=7.5 Hz, 2H), 7.13 (m, 2H), 7.27 (m, 6H), 7.44 (m, 8H), 7.50 (m, 2H), 7.57 (m, 4H); NMR (100 MHz, CDCl$_3$, δ): 29.9, 68.4, 71.5, 120.7 (2 C), 127.4 (2 C), 128.6-131.1 (24 C), 137.1 (2 C), 137.2 (2 C), 138.4 (2 C), 150.2 (2 C); IR (cm$^{-1}$): 3534, 3270, 3058, 2869, 1601, 1457, 1427, 1225, 1077, 949.

Zr complex (8):
Ligand (7) (103 mg, 173 mmol) was dissolved in 5 mL of toluene and cooled to −35° C. A solution of dibenzylzirconium dichloride (68 mg, 173 mmol) in 5 mL of toluene was added to the ligand solution and the mixture was heated at 85° C. for 2 h. A white precipitate was formed, collected and washed with hexane. Two isomers were observed by NMR in an approximate 7:3 ratio: $^1$H NMR (400 MHz, CDCl$_3$, δ): Major isomer: 1.83 (m, 2H), 3.33 (m, 2H), 3.90 (d, J=9.2 Hz, 2H), 4.03 (m, 2H), 4.73 (d, J=9.2 Hz, 2H), 6.88-7.68 (m, 24H). Minor isomer: 2.5 (m, 2H), 4.33 (m, 2H), 4.56 (d, J=12.4 Hz, 2H), 4.62 (m, 2H), 5.35 (d, J=12.8 Hz, 2H), 6.88-7.68 (m, 24H).

1,4-bis((2-bromobenzyl)oxy)butane (9)

Butanediol (901 mg, 10 mmol) was dissolved in 10 mL THF and added to a suspension of sodium hydride (808 mg of 60% on mineral oil, washed with pentane, 20.2 mmol) in 20 mL THF. It was stirred for 10 min before adding 2-bromobenzylbromide (5 g, 20 mmol) and TBAI (approx. 100 mg). The reaction was heated at 70° C. overnight, then quenched with 10% HCl and extracted with ether. The organic portions were washed with brine, dried (MgSO$_4$), filtered, and concentrated to give the product as a pale yellow solid in 86% yield: mp 57.9-58.8° C.; $^1$H NMR (400 MHz, CDCl$_3$, δ): 1.79 (m, 4H), 3.60 (m, 4H), 4.57 (s, 4H), 7.14 (m, 2H), 7.31 (m, 2H), 7.47 (m, 4H); $^{13}$C NMR (100 MHz, CDCl$_3$, δ): 26.8 (2 C), 70.9 (2 C), 72.4 (2 C), 122.8-133.7 (10 C), 138.2 (2 C); IR (cm$^{-1}$): 3464, 3064, 2939, 2860, 1568, 1469, 1440, 1357, 1102, 1027.

2,2'''-((butane-1,4-diylbisoxy)bismethylene)bis([1,1': 3',1''-terphenyl]-2'-ol)) (10)

The phenyl phenol lithium salt (1.52 g, 5.06 mmol) was dissolved in 100 mL of THF and cooled to −70° C. Zinc dichloride (960 mg, 6.07 mmol) was added and the reaction warmed to ambient temperature for 1 h. The above bisbromobenzyloxybenzene (1.0 g, 2.3 mmol) and bis(tri-tert-butylphosphine)palladium (24 mg, 0.04 mmol) were added and the reaction heated at reflux overnight. After cooling, the reaction was quenched with water and extracted with 3 portions of ether. Combined organic layers were washed with brine, dried (MgSO$_4$), filtered, and concentrated under reduced pressure. The crude oil was redissolved in THF/ethanol (1:1), PTSA (approx. 100 mg) was added and the solution heated at 80° C. overnight. Volatiles were removed under reduced pressure and the resulting brown oil was purified by passage through a silica gel plug with 10% acetone/hexane as eluent. The product was obtained as a white solid in 36% yield: $^1$H NMR (500 MHz, CDCl$_3$, δ): 1.57 (br S, 4H), 3.34 (br s, 4H), 4.34 (m, 4H), 5.8 (s, 2H), 7.06 (t, J=7.5 Hz, 2H), 7.13 (m, 2H), 7.35 (m, 6H), 7.43 (m, 8H), 7.56 (m, 6H); NMR (125 MHz, CDCl$_3$, δ): 26.3 (2 C), 70.84 (2 C), 71.48 (2 C), 120.7 (2 C), 127.4 (2 C), 128.6-129.7 (18 C), 130.2 (2 C), 130.5 (2 C), 131.1 (2 C), 137.1 (2 C), 137.2 (2 C), 138.4 (2 C), 150.3; IR (cm$^{-1}$): 3533, 3279, 3058, 2939, 2868, 1457, 1427, 1226, 1075, 909.

Zr Complex (11):
The above ligand (10) was subjected to similar metalation procedures as described above.

1,2-bis(2-bromobenzyloxy)benzene (12)

Bromobenzylbromide (11.2 g, 44.8 mmol), catechol (2.46 g, 22.4 mmol), powdered potassium carbonate (7.43 g, 53.7 mmol), and TBAI (approx. 100 mg) were dissolved in 115 mL of acetonitrile and heated at 70° C. overnight. The reaction was cooled and filtered. The filtrate was condensed to a pale yellow oil which turned solid upon standing and was used without further purification: mp 58.1-59.5° C.; $^1$H NMR (500 MHz, CDCl$_3$, δ): 5.26 (s, 4H), 6.97 (m, 4H), 7.19 (m, 2H), 7.33 (m, 2H), 7.59 (d, J=8.0 Hz, 2H), 7.67 (d, J=8.5 Hz, 2H); $^{13}$C NMR (125 MHz, CDCl$_3$, δ): 70.8 (2 C), 115.2 (2 C), 122.1 (2 C), 122.2 (2 C), 127.7 (2 C), 129.0 (2 C), 129.3 (2 C), 132.7 (2 C), 136.8 (2 C), 148.9 (2 C).

2,2'''-((1,2-phenylenebisoxy)bismethylene)bis([1,1': 3',1''-terphenyl]-2'-ol) (13)

The phenyl phenol lithium salt (1.27 g, 4.9 mmol) was dissolved in 100 mL of THF and cooled to −70° C. Zinc dichloride (800 mg, 5.88 mmol) was added and the reaction warmed to ambient temperature for 1 h. The above bisbromobenzyloxy-benzene (12) (1 g, 2.23 mmol) and bis(tri-tert-butylphosphine)palladium (23 mg, 0.04 mmol) were added and the reaction heated at reflux overnight. After cooling, the reaction was quenched with water and extracted with 3 portions of ether. Combined organic layers were washed with brine, dried (MgSO$_4$), filtered and concentrated under reduced pressure. The crude oil was redissolved in THF/ethanol (1:1), PTSA (approx. 100 mg) was added and the solution heated at 80° C. overnight. Volatiles were removed under reduced pressure and the resulting crude oil purified by passage through a silica gel plug with 10% acetone/hexane as eluent giving the product as a white powder: mp 66.0-67.4° C.; $^1$H NMR (500 MHz, CDCl$_3$, δ): 5.00 (m, 4H), 5.32 (s, 2H), 6.72 (m, 2H), 6.78 (m, 2H), 7.02 (m, 2H), 7.14 (m, 2H), 7.42 (m, 14H), 7.50 (m, 4H), 7.63 (m, 2H); $^{13}$C NMR (125 MHz, CDCl$_3$, δ): 69.6 (2 C), 115.4 (2 C), 120.9 (2 C), 121.9 (2 C), 127.7-130.8 (28 C), 136.4 (2 C), 137.9 (2 C), 149.1 (2 C), 150.0 (2 C); IR (cm$^{-1}$): 3531, 3444, 3059, 3030, 1591, 1500, 1455, 1427, 1324, 1249, 1222, 1123, 1010, 887.

Zr Complex (14):

Ligand (13) (145 mg, 231 mmol) was dissolved in 5 mL of toluene and cooled to −35° C. A solution of dibenzylzirconium dichloride (91 mg, 231 mmol) in 5 mL of toluene was added to the ligand solution and the mixture was heated at 85° C. for 2 h. A white precipitate was formed, collected and washed with hexane: $^1$H NMR (500 MHz, tol-d$_9$, δ): 4.79 (m, 4H), 6.61 (m, 4H), 6.85 (m, 2H), 7.17 (m, 16H), 7.42 (m, 4H), 7.54 (m, 2H).

2,2'-(((4-(tert-butyl)-1,2-phenylene)bisoxy)bismethylene)bis(bromobenzene) (15)

Bromobenzylbromide (11.2 g, 44.8 mmol), tert-butyl catechol (3.7 g, 22.4 mmol), powdered potassium carbonate (7.43 g, 53.7 mmol), and TBAI (approx. 100 mg) were dissolved in 115 mL of acetonitrile and heated at 70° C. overnight. The reaction was cooled and filtered. The filtrate was condensed giving the product as a white solid and was used without further purification: R$_f$ 0.51 (20:80 acetone/isohexane); mp 78.9-80.0° C.; $^1$H NMR (500 MHz, CDCl$_3$, δ): 1.30 (s, 9H), 5.23 (s, 2H), 5.28 (s, 2H), 6.95 (m, 2H), 7.04 (d, J=2.0 Hz, 1H), 7.18 (m, 2H), 7.33 (t, J=7.5 Hz, 2H), 7.58 (m, 2H), 7.69 (m, 2H); $^{13}$C NMR (125 MHz, CDCl$_3$, δ): 31.6 (3 C), 70.9, 71.2, 114.0, 114.7, 118.8, 122.2, 122.4, 127.7 (2 C), 129.1, 129.2, 129.3, 129.4, 132.6 (2 C), 137.0, 137.1, 145.3, 146.9, 148.2; IR (cm$^{-1}$): 3424, 3063, 2865, 1568, 14671440, 1126, 1026, 892.

2,2'''-(((4-(tert-butyl)-1,2-phenylene)bisoxy)bismethylene)bis ([1,1':3',1''-terphenyl]-2'-ol) (16)

The phenyl phenol lithium salt (1.5 g, 5.7 mmol) was dissolved in 100 mL of THF and cooled to −70° C. Zinc dichloride (940 mg, 6.8 mmol) was added and the reaction warmed to ambient temperature for 1 h. The above bisbromo compound (15) (1.32 g, 2.6 mmol) and bis(tri-tert-butylphosphine)palladium (26 mg, 0.05 mmol) were added and the reaction heated at reflux overnight. After cooling, the reaction was quenched with water and extracted with 3 portions of ether. Combined organic layers were washed with brine, dried (MgSO$_4$), filtered and concentrated under reduced pressure. The crude oil was redissolved in THF/ethanol (1:1), PTSA (approx. 100 mg) was added and the solution heated at 80° C. overnight. Volatiles were removed under reduced pressure and the resulting crude oil purified by passage through a silica gel plug with 10% acetone/hexane as eluent giving the product as a white powder: mp 171.1-174.8° C.; $^1$H NMR (500 MHz, CDCl$_3$, δ): 1.17 (s, 9H), 4.97 (m, 4H), 5.35 (d, J=19.5 Hz, 2H), 6.64 (m, 1H), 6.75 (s, 1H), 6.81 (m, 1H), 7.05 (m, 2H), 7.15 (m, 2H), 7.39 (m, 14H0, 7.51 (m, 4H), 7.62 (m, 2H); IR (cm$^{-1}$): 3535, 3443, 3058, 2961, 1601, 1505, 1427, 1223, 885.

Zr Complex (17):

Ligand (16) (134 mg, 196 mmol) was dissolved in 5 mL of toluene and cooled to −35° C. A solution of dibenzylzirconium(IV) chloride (66 mg, 196 mmol) in 5 mL of toluene was added to the ligand solution and the mixture was heated at 85° C. for 2 h. The solution was concentrated, redissolved in about 1 mL of toluene, and then precipitated out in pentane. The pale yellow solid was collected and washed with pentane: $^1$H NMR (400 MHz, CD$_2$Cl$_2$, δ): 1.39 (s, 9H), 5.14 (m, 2H), 5.42 (m, 1H), 5.62 (m, 1H), 6.05 (d, J=7.2 Hz, 1H), 7.03-7.59 (m, 23H).

2,2'-(oxybismethylene)bis(bromobenzene) (18)

Bromobenzaldehyde (5.0 g, 27 mmol) and BiCl$_3$ (930 mg, 2.9 mmol) were dissolved in 75 mL of methylene chloride. Triethylsilane (5.5 mL, 35 mmol) was added slowly and the solution stirred at ambient temperature overnight. The reaction was quenched with saturated ammonium chloride and extracted twice with methylene chloride. The combined organic layers were dried (MgSO$_4$), filtered, and concentrated to give an oily crystalline solid. The product was purified by passage through a silica gel plug (10% acetone/isohexane) and recrystallization: R$_f$=0.53 (20:80 acetone/isohexane); $^1$H NMR (400 MHz, CDCl$_3$, δ): 4.74 (s, 4H), 7.18 (m, 2H), 7.35 (m, 2H), 7.47 (m, 4H); $^{13}$C NMR (125 MHz, CDCl$_3$, δ): 72.3 (2 C), 122.9 (2 C), 127.7 (2 C), 129.2 (2 C), 129.3 (2 C), 132.8 (2 C), 137.7 (2 C); IR (cm$^{-1}$): 3062, 2868, 1592, 1468, 1439, 1352, 1205, 1122, 1099, 1025.

2,2'''-(oxybismethylene)bis([1,1':3',1''-terphenyl]-2'-ol) (19)

The phenyl phenol lithium salt (1.61 g, 6.16 mmol) was dissolved in 100 mL of THF and cooled to −70° C. Zinc dichloride (800 mg, 7.39 mmol) was added and the reaction warmed to ambient temperature for 1 h. The above bisbromobenzyloxybenzene (1.0 g, 2.8 mmol) and bis(tri-tert-butylphosphine)palladium (28 mg, 0.05 mmol) were added and the reaction heated at reflux overnight. After cooling, the reaction was quenched with water and extracted with 3 portions of ether. Combined organic layers were washed with brine, dried (MgSO$_4$), filtered, and concentrated under reduced pressure. The crude oil was redissolved in THF/ethanol (1:1); PTSA (approx. 100 mg) was added and the solution heated at 80° C. overnight. The solution was concentrated to an oil, then purified by passage through a silica plug (10% acetone/isohexane) giving the product as a white powder: mp 124.0-126.5° C.; $^1$H NMR (500 MHz, tol-d$_8$, 363 K, 6): 4.25 (s, 4H), 5.26 (s, 2H), 6.83 (t, J=7.5 Hz, 2H), 6.94 (dd, J=2.0, 7.5 Hz, 2H), 7.11 (m, 8H), 7.21 (m, 6H), 7.35 (m, 2H), 7.47 (m, 4H); $^{13}$C NMR (125 MHz, CDCl$_3$, δ): 71.2 (2 C), 120.7 (2 C), 127.5 (2 C), 128.6-130.9 (26 C), 137.0 (2 C), 138.2 (2 C), 150.1 (2 C); IR (cm$^{-1}$): 3534, 3339, 3058, 2933, 2870, 1601, 1427, 1325, 1224, 1073, 950.

Zr Complex (20):

The dibenzyloxy ligand (118 mg, 220 mmol) was dissolved in toluene and cooled to −35° C. A solution of dibenzylzirconium dichloride (86 mg, 220 mmol) in 5 mL of toluene was added to the ligand solution and the mixture was heated at 85° C. for 2 h. A white precipitate was formed, collected and washed with hexane: $^1$H NMR (500 MHz, CD$_2$Cl$_2$, δ): 4.59 (br m, 2H), 5.01 (br m, 2H), 7.00 (m, 4H), 7.12 (m, 2H), 7.18 (m, 2H), 7.44 (m, 12H), 7.64 (m, 4H).

2-((5-methyl-[1,1':4',1''-terphenyl]-2-yl)oxy)tetrahydro-2H-pyran (21)

2-(p-tolyloxy)tetrahydro-2H-pyran was dissolved in ether and ortho-lithiated by treatment with 1 equiv. of 2.5 M n-BuLi as described previously. The resulting lithium salt (1.0 g, 5.0 mmol) was dissolved in 15 mL of THF with zinc chloride (825 mg, 6 mmol). After 30 min at ambient temperature, diphenyl bromide (1.17 g, 5.0 mmol) and bis(tri-tert-butylphosphine)palladium (50 mg, 0.1 mmol) were added and the reaction stirred overnight. The reaction was then quenched with water and extracted with 3 portions of ether. Combined organic layers were washed with brine, dried (MgSO$_4$), filtered, and concentrated under reduced pressure. Purification was achieved by passage through an alumina plug using 10% acetone/isohexane as eluent: $^1$H NMR (400 MHz, CDCl$_3$, δ): 1.98 (m, 6H), 2.29 (s, 3H), 3.69 (m, 1H), 3.95 (m, 1H), 5.48 (t, J=3.2 Hz, 1H), 7.21 (m, 1H), 7.33 M, 1H), 7.44 (m, 1H), 7.48 (m, 1H), 7.58 (m, 2H), 7.77 (m, 6H).

2,2""-((propane-1,3-diylbis(oxy))bis(methylene))bis (5'-methyl-[1,1':3',1":4",1'"-quaterphenyl]-2'-ol) (22))

To the above compound (21) (2.92 g, 8.0 mmol) dissolved in pentane was added n-BuLi (3.4 mL, 2.5 M in hexane). The reaction was stirred for 2 h and the precipitate collected and washed with pentane. This lithium salt (1.83 g, 5.2 mmol) was then dissolved with zinc chloride (850 mg, 6.2 mmol) in THF. After 20 min, 1,3-bis((2-bromobenzyl)oxy) propane (1.0 g, 4.8 mmol) and bis(tri-tert-butylphosphine) palladium (53 mg, 0.1 mmol) were added and the reaction stirred overnight. The reaction was then quenched with water and extracted with 3 portions of ether. Combined organic layers were washed with brine, dried (MgSO$_4$), filtered, and concentrated under reduced pressure. The crude oil was redissolved in THF/ethanol (1:1), PTSA (approx. 100 mg) was added and the solution heated at 70° C. overnight. Volatiles were removed under reduced pressure and the resulting brown oil was purified by passage through a silica gel plug with 10% acetone/hexane as eluent. The product was obtained as a white solid: $^1$H NMR (500 MHz, CDCl$_3$, δ): 1.79 (m, 2H), 2.34 (s, 6H), 3.46 (app br s, 4H), 4.30 (m, 4H), 5.74 (s, 2H), 6.90 (s, 2H), 7.18 (s, 2H), 7.38 (m, 14H0, 7.62 (m, 12H); $^{13}$C NMR (125 MHz, CDCl$_3$, δ): 20.68, 20.77, 29.9, 68.1 (2 C), 71.6 (2 C), 127.2-131.1 (36 C), 136.9 (2 C), 137.4 (2 C), 137.6 (2 C), 140.0 (2 C), 141.1 (2 C), 148.1 (2 C); IR (cm$^{-1}$): 3537, 3284, 3027, 2919, 2867, 1463, 1227, 1077, 950, 908, 841.

2-((2',5,5'-trimethyl-[1,1'-biphenyl]-2-yl)oxy)tetra-hydro-2H-pyran

Prepared from 2-(p-tolyloxy)tetrahydro-2H-pyran (3.0 g, 15 mmol) and 2,5-dimethylphenyl bromide (2.1 mL, 15 mmol).

2",2""-((propane-1,3-diylbis(oxy))bis(methylene)) bis(2,5,5'-trimethyl-[1,1':3',1"-terphenyl]-2'-ol) (23)

Prepared from the above compound and 1,3-bis((2-bromobenzyl)oxy)propane using the procedure described for compound (22). $^1$H NMR (500 MHz, CDCl$_3$, δ): 1.82 (m, 2H), 2.21 (s, 6H), 2.36 (s, 6H), 2.37 (s, 6H), 3.49 (br s, 2H), 4.36 (br m, 4H), 5.27 (br s, 2H), 7.00 (d, J=5.0 Hz, 4H), 7.11 (m, 4H), 7.19 (m, 2H), 7.40 (m, 4H), 7.54 (m, 4H), 7.56 (m, 2H); $^{13}$C NMR (125 MHz, CDCl$_3$, δ): 19.6 (2 C), 20.7 (2 C), 21.1 (2 C), 31.1, 68.0 (2 C), 71.2 (2 C), 115.2 (2 C), 128.1-137.4 (32 C), 147.9 (2 C).

General Procedure for Supporting Catalysts:

The zirconium complex, typically between 15 to 30 mg, was dissolved in toluene and a solution of MAO (Albemarle, 30 wt. %). Silica gel (757 previously dehydrated at 600° C.) was added and the slurry stirred until completely mixed, approx. 5 min. Toluene was then removed under vacuum and the supported catalyst tested in a batch reactor.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

All documents cited are herein fully incorporated by reference for all jurisdictions in which such incorporation is permitted and to the extent such disclosure is consistent with the description of the present disclosure.

What is claimed is:

1. A bridged bi-aromatic phenol ligand of formula (I):

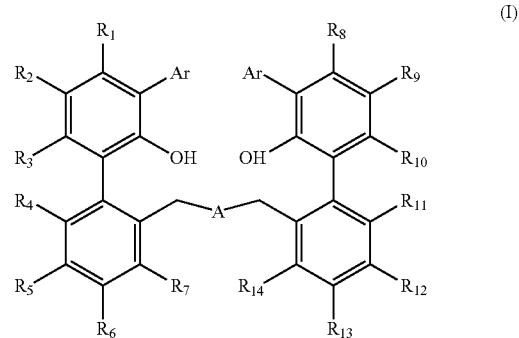

wherein each of R$^1$, R$^2$, R$^3$, R$^4$, R$^5$, R$^6$, R$^7$, R$^8$, R$^9$, R$^{10}$, R$^{11}$, R$^{12}$, R$^{13}$ and R$^{14}$ is independently selected from the group consisting of hydrogen, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is O, S, NR$^a$ wherein R$^a$ is optionally substituted hydrocarbyl, or A is —Y-E-Y'— wherein E is a bridging group having from one to 50 non-hydrogen atoms and Y and Y' are independently selected from O, S, NR$^a$ and PR$^a$ and A is O, S, NR$^a$ and PR$^a$ wherein R$^a$ is optionally substituted hydrocarbyl, or A is —Y-E-Y'— wherein E is a bridging group having from one to 50 non-hydrogen atoms; Y and Y' are independently selected from O, S, NR$^a$ and PR$^a$ wherein R$^a$ is optionally substituted hydrocarbyl wherein R$^a$ is optionally substituted hydrocarbyl; Ar is, independently, optionally substituted aryl or optionally substituted heteroaryl.

2. A ligand according to claim 1 wherein each of R$^1$, R$^2$, R$^3$, R$^4$, R$^5$, R$^6$, R$^7$, R$^8$, R$^9$, R$^{10}$, R$^{11}$ R$^{12}$, R$^{13}$ and R$^{14}$ is independently selected from the group consisting of hydrogen, halide, and optionally substituted alkyl, heteroalkyl, aryl, heteroaryl, alkoxyl, aryloxyl, silyl, dialkylamino, alkylthio, and arylthio.

3. A ligand according to claim 1 wherein each of R$^1$, R$^2$, R$^3$, R$^4$, R$^5$, R$^6$, R$^7$, R$^8$, R$^9$, R$^{10}$, R$^{11}$ R$^{12}$, R$^{13}$ and R$^{14}$ is independently selected from the group consisting of hydrogen, halide, and optionally substituted alkyl, heteroalkyl, aryl, heteroaryl, alkoxyl, and aryloxyl.

4. A ligand according to claim 1 wherein the bridging group E is selected from the group consisting of optionally substituted divalent hydrocarbyl and divalent heteroatom containing hydrocarbyl.

5. A ligand according to claim 1 wherein the bridging group E is selected from the group consisting of optionally substituted divalent alkyl, alkenyl, alkynyl, heteroalkyl, heteroalkenyl, heteroalkynyl, carbocycle, heterocarbocycle, aryl, heteroaryl and silyl.

6. A ligand according to claim 1 wherein the bridging group E is represented by the general formula -$(QR^{15}_{2-z''})_{z'}$— wherein each Q is either carbon or silicon and each $R^{15}$ may be the same or different from the others such that each $R^{15}$ is selected from the group consisting of hydrogen and optionally substituted hydrocarbyl and heteroatom containing hydrocarbyl, and optionally two or more $R^{15}$ groups may be joined into a ring structure having from 3 to 50 atoms in the ring structure not counting hydrogen atoms; z' is an integer from 1 to 10; and z'' is 0, 1 or 2.

7. A ligand according to claim 1 wherein Ar is, independently, an optionally substituted phenyl, naphthyl, biphenyl, anthracenyl or phenanthrenyl.

8. A ligand according to claim 1 wherein Ar is, independently, an optionally substituted thiophene, pyridine, isoxazole, pyrazole, pyrrole, furan, or benzo-fused analogues of these rings.

9. A ligand according to claim 1 wherein each occurrence of Ar is the same.

10. A ligand according to claim 1 wherein the ligand of formula (I) is of formula (II):

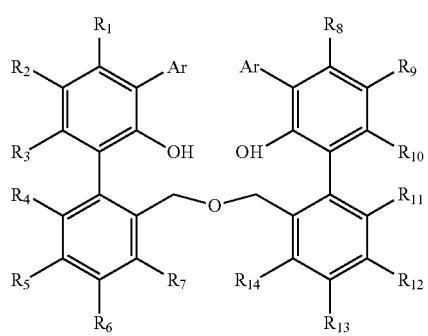

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, and Ar is as defined in claim 1.

11. A ligand according to claim 1 wherein the ligand of formula (I) may be of formula (III):

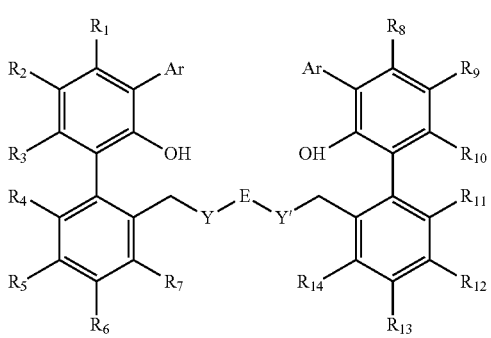

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, Ar, Y' and E is as defined in claim 1.

12. A ligand according to claim 1 wherein the ligand of formula (I) may be of formula (IV):

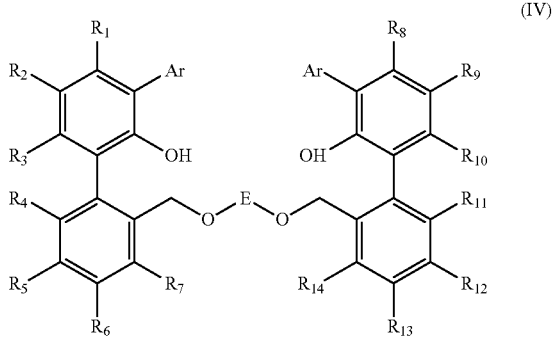

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, Ar, and E is as defined in claim 1.

13. A method of preparing a bridged bi-aromatic phenol ligand according to claim 1 comprising:

deprotecting a compound of formula (VIII)

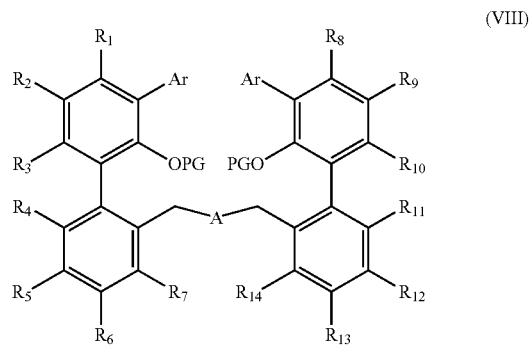

to yield the bi-aromatic phenol ligand of formula (I) according to claim 1; wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydrogen, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is O, S, $NR^a$ and $PR^a$ wherein $R^a$ is optionally substituted hydrocarbyl, or A is —Y-E-Y'— wherein E is a bridging group having from one to 50 non-hydrogen atoms; Y and Y' are independently selected from O, S, $NR^a$ and $PR^a$ wherein $R^a$ is optionally substituted hydrocarbyl; Ar is optionally substituted aryl or heteroaryl; and PG is a protecting group.

14. A method according to claim 13 comprising the steps of:

a) treating a protected bi-aromatic phenol of formula (V) with a lithiating agent to yield a dilithio protected bi-aromatic phenol of formula (VI);

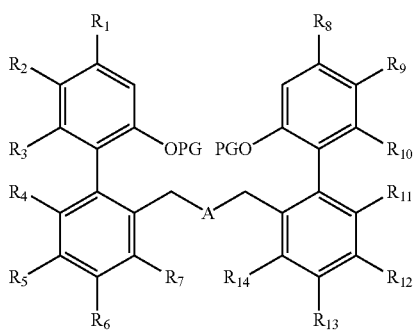
(V)

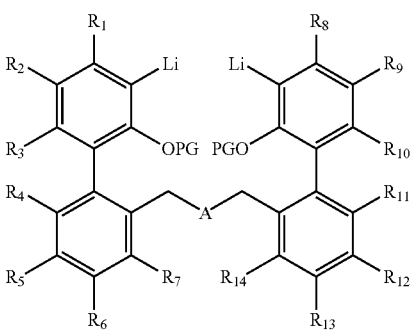
(VI)

b) treating the dilithio protected bi-aromatic phenol of formula (VI) with a zinc compound and a compound of formula ArX in the presence of a catalyst, to yield the protected bi-aromatic phenol of formula (VIII)

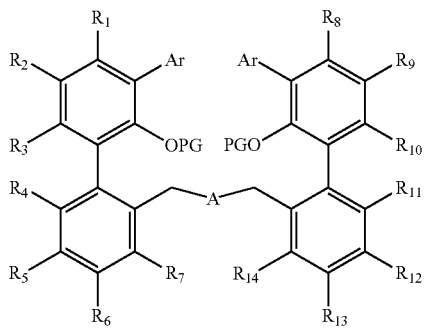
(VIII)

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydrogen, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more $R^1$ to $R^{14}$ groups can combine together into ring structures with such ring structures having from 3 to 100 non-hydrogen atoms in the ring; A is O, S, $NR^a$ and $PR^a$ wherein $R^a$ is optionally substituted hydrocarbyl, or A is —Y-E-Y'— wherein E is a bridging group having from one to 50 non-hydrogen atoms; Y and Y' are independently selected from O, S, $NR^a$ and $PR^a$ wherein $R^a$ is optionally substituted hydrocarbyl; Ar is optionally substituted aryl or heteroaryl; X is halide; PG is a protecting group.

15. A method according to claim 13 comprising the steps of:
a) treating a compound of formula (X) with a zinc halide and a compound of formula ArX in the presence of a catalyst to yield a compound of formula (XI);

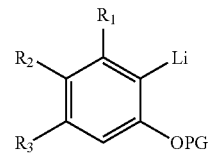
(X)

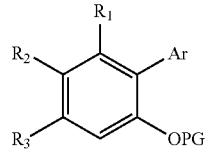
(XI)

b) treating the compound of formula (XI) with a lithiating agent to yield a compound of formula (XII);

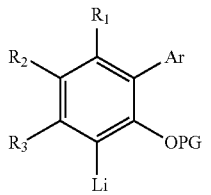
(XII)

c) treating the compound of formula (XII) with zinc halide and a compound of formula (XIII) in the presence of a catalyst to yield the compound of formula (VIII); and

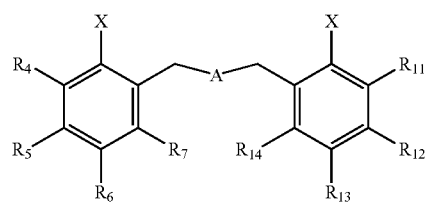
(XIII)

d) deprotecting the compound of formula (VIII) to yield the bi-aromatic phenol ligand of formula (I)
wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from the group consisting of hydrogen, halide, optionally substituted hydrocarbyl, heteroatom-containing optionally substituted hydrocarbyl, alkoxy, aryloxy, silyl, boryl, dialkyl amino, alkylthio, arylthio and seleno; optionally two or more R groups can combine together into ring structures with such ring structures having from 3 to 100 non-hydrogen atoms in the ring; A is O, S, $NR^a$ and $PR^a$ wherein $R^a$ is optionally substituted hydrocarbyl, or A is —Y-E-Y'— wherein E is a bridging group having from one to 50 non-hydrogen atoms; Y and Y' are independently selected from O, S, $NR^a$ and $PR^a$ wherein $R^a$ is optionally substituted hydrocarbyl; Ar is optionally substituted aryl or heteroaryl; X is halide; PG is a protecting group.

16. A method according to claim 13 wherein each of $R^1$, $R^2$, $R^3$, $R^4$, $R^5$, $R^6$, $R^7$, $R^8$, $R^9$, $R^{10}$, $R^{11}$ $R^{12}$, $R^{13}$ and $R^{14}$ is independently selected from the group consisting of hydrogen, halide, and optionally substituted alkyl, heteroalkyl, aryl, heteroaryl, alkoxyl, aryloxyl, silyl, dialkylamino, alkylthio, and arylthio.

17. A method according to claim 13 wherein each of $R^1$, $R^2$, $R^3$, $R^4$, $R^5$, $R^6$, $R^7$, $R^8$, $R^9$, $R^{10}$, $R^{11}$ $R^{12}$, $R^{13}$ and $R^{14}$ is independently selected from the group consisting of hydrogen, halide, and optionally substituted alkyl, heteroalkyl, aryl, heteroaryl, alkoxyl, and aryloxyl.

18. A method according to claim 13 wherein the bridging group E is selected from the group consisting of optionally substituted divalent hydrocarbyl and divalent heteroatom containing hydrocarbyl.

19. A method according to claim 13 wherein the bridging group E is selected from the group consisting of optionally substituted divalent alkyl, alkenyl, alkynyl, heteroalkyl, heteroalkenyl, heteroalkynyl, carbocycle, heterocarbocycle, aryl, heteroaryl and silyl.

20. A method according to claim 13 wherein the bridging group E is represented by the general formula $-(QR^{15}_{2-z''})_{z'}-$ wherein each Q is either carbon or silicon and each $R^{15}$ may be the same or different from the others such that each $R^{15}$ is selected from the group consisting of hydrogen and optionally substituted hydrocarbyl and heteroatom containing hydrocarbyl, and optionally two or more $R^{15}$ groups may be joined into a ring structure having from 3 to 50 atoms in the ring structure not counting hydrogen atoms; $z'$ is an integer from 1 to 10; and $z''$ is 0, 1 or 2.

* * * * *